US007994399B2

(12) United States Patent
Lai et al.

(10) Patent No.: US 7,994,399 B2
(45) Date of Patent: Aug. 9, 2011

(54) **METHODS FOR THE PRODUCTION OF STABLY TRANSFORMED, FERTILE *ZEA MAYS* PLANTS**

(75) Inventors: Fang-Ming Lai, Cary, NC (US); Penny Mrabet, Cary, NC (US); Kangfeng Mei, Apex, NC (US); Luke Mankin, Raleigh, NC (US); Hongyi Zhang, Green Park, MO (US); Christopher Bagley, Youngsville, NC (US); Larry Nea, Raleigh, NC (US); Zhongqi Wang, Cary, NC (US); Bijay Singh, Cary, NC (US); Jianying Peng, Durham, NC (US)

(73) Assignee: BASF Plant Science GmbH, Ludwigshafen (DE)

( * ) Notice: Subject to any disclaimer, the term of this patent is extended or adjusted under 35 U.S.C. 154(b) by 708 days.

(21) Appl. No.: 11/922,828

(22) PCT Filed: Jun. 22, 2006

(86) PCT No.: PCT/EP2006/063448
§ 371 (c)(1),
(2), (4) Date: Dec. 20, 2007

(87) PCT Pub. No.: WO2006/136596
PCT Pub. Date: Dec. 28, 2006

(65) Prior Publication Data
US 2009/0249514 A1 Oct. 1, 2009

Related U.S. Application Data

(60) Provisional application No. 60/693,321, filed on Jun. 23, 2005.

(51) Int. Cl.
*C12N 15/84* (2006.01)
*A01H 1/00* (2006.01)
*A01H 5/00* (2006.01)
*A01H 4/00* (2006.01)

(52) U.S. Cl. ............... 800/294; 800/275; 800/320.1; 435/424; 435/430.1; 435/431; 435/469

(58) Field of Classification Search ............... None
See application file for complete search history.

(56) References Cited

U.S. PATENT DOCUMENTS

| | | | |
|---|---|---|---|
| 5,290,753 | A | 3/1994 | Newhouse et al. |
| 5,591,616 | A | 1/1997 | Hiei et al. |
| 5,767,361 | A | 6/1998 | Dietrich |
| 5,981,840 | A * | 11/1999 | Zhao et al. ............ 800/294 |
| 6,420,630 | B1 | 7/2002 | Wilson et al. |
| 6,653,529 | B2 | 11/2003 | Peng et al. |
| 7,759,545 | B2 * | 7/2010 | Lowe et al. ............ 800/275 |
| 2003/0046724 | A1 | 3/2003 | Ranch et al. |
| 2004/0016030 | A1 | 1/2004 | Lowe et al. |

FOREIGN PATENT DOCUMENTS

| | | |
|---|---|---|
| EP | 0672752 A1 | 9/1995 |
| EP | 0709462 A2 | 5/1996 |
| WO | WO-94/00977 | 1/1994 |
| WO | WO-95/06722 | 3/1995 |
| WO | WO-98/08963 A1 | 3/1998 |
| WO | WO-98/32326 A2 | 7/1998 |
| WO | WO-98/39419 A1 | 9/1998 |
| WO | WO-01/09302 A2 | 2/2001 |

OTHER PUBLICATIONS

Frame, B. R., et al., "*Agrobacterium tumefaciens*-Mediated Transformation of Maize Embryos Using a Standard Binary Vector System", Plant Physiology, 2002, vol. 129, pp. 13-22.

Zhao, Z-Y, et al., "High Throughput Genetic Transformation Mediated by *Agrobacterium tumefaciens* in Maize", Molecular Breeding, 2002, vol. 8, No. 4, pp. 323-333.

Cheng, M., et al., "Invited Review: Factors Influencing *Agrobacterium*-Mediated Transformation of Monocotyledonous Species", In Vitro Cell. Dev. Biol.—Plant, 2004, vol. 40, pp. 31-45.

Armstrong, C. L., et al., "Establishment and Maintenance of Friable, Embryogenic Maize Callus and the Involvment of $_L$-Proline", Planta, 1985, vol. 164, No. 2, pp. 207-214.

Ishida, Y., et al., "High Efficiency Transformation of Maize (*Zea mays* L.) Mediated by *Agrobacterium tumefaciens*", Nature Biotechnology, 1996, vol. 14, pp. 745-750.

Hiei, Y., et al., "Efficient Transformation of Rice (*Oryza sativa* L.) Mediated by *Agrobacterium* and Sequence Analysis of the Boundaries of the T-DNA", The Plant Journal, 1994, vol. 6, No. 2, pp. 271-282.

Potrykus, I., "Gene Transfer to Cereals: An Assessment", Bio/Technology, 1990, vol. 8, pp. 535-542.

Raineri, D. M., et al., "*Agrobacterium*-Mediated Transformation of Rice (*Oryza sativa* L.)", Bio/Technology, 1990, vol. 8, pp. 33-38.

Mooney, P. A., et al., "*Agrobacterium tumefaciens*-gene Transfer Into Wheat Tissues", Plant Cell Tissue & Organ Culture, 1991, vol. 25, pp. 209-218.

Gould, J., et al., "Transformation of *Zea mays* L. Using *Agrobacterium tumefaciens* and the Shoot Apex", Plant Physiol., 1991, vol. 95, pp. 426-434.

Livingstone, D. M., et al., "Efficient Transformation and Regeneration of Diverse Cultivars of Peanut (*Arachis hypogaea* L.) by Particle Bombardment into Embryogenic Callus Produced from Mature Seeds", Molecular Breeding, 1999, vol. 5, pp. 43-51.

François, I. E. J. A., et al., "Different Approaches for Multi-Transgene-Stacking in Plants", Plant Science, 2002, vol. 163, pp. 281-295.

(Continued)

*Primary Examiner* — David T Fox
(74) *Attorney, Agent, or Firm* — Connolly Bove Lodge & Hutz, LLP

(57) ABSTRACT

The present invention relates to improved methods for the incorporation of DNA into the genome of a *Zea mays* plant by means of *Agrobacterium*-mediated transformation. Preferred is the use of the *Zea may* lines deposited with American Type Culture Collection under the Patent Deposit Designation PTA-6170 and PTA-6171.

17 Claims, No Drawings

OTHER PUBLICATIONS

Newhouse, K., et al., "Mutations in Corn (*Zea mays* L.) Conferring Resistance to Imidazolinone Herbicides", Theor. Appl. Genet., 1991, vol. 83, pp. 65-70.

Halpin, C., "Gene Stacking in Transgenic Plants—the Challenge for 21st Century Plant Biotechnology", Plant Biotechnology Journal, 2005, vol. 3, pp. 141-155.

Tan, S., et al., "Imidazolinone-Tolerant Crops; History, Current Status and Future", Pest Management Science, 2005, vol. 61, pp. 246-257.

Ray, K., et al., "Mutant *Acetolactate Synthase* Gene is an Efficient in Vitro Selectable Marker for the Genetic Transformation of *Brassica juncea* (Oilseed Mustard)", Journal of Plant Physiology, 2004, vol. 161, pp. 1079-1083.

Ebinuma, H., et al., "Selection of Marker-Free Transgenic Plants Using the Isopentenyl Transferase Gene", Proc. Natl. Acad. Sci. U.S.A., 1997, vol. 94, pp. 2117-2121.

Wright, T. R., et al., "Corn (*Zea mays*) Acetolactate Synthase Sensitivity to Four Classes of ALS-Inhibiting Herbicide", Weed Science, 1998, vol. 46, pp. 8-12.

* cited by examiner

METHODS FOR THE PRODUCTION OF STABLY TRANSFORMED, FERTILE ZEA MAYS PLANTS

RELATED APPLICATIONS

This application is a national stage application (under 35 U.S.C. 371) of PCT/EP2006/063448 filed Jun. 22, 2006, which claims benefit of U.S. provisional application 60/693,321 filed Jun. 23, 2005.

BACKGROUND OF THE INVENTION

1. Field of the Invention

The present invention relates to improved methods for the incorporation of DNA into the genome of a *Zea mays* plant by means of *Agrobacterium*-mediated transformation.

2. Description of the Related Art

During the past decade, it has become possible to transfer genes from a wide range of organisms to crop plants by recombinant DNA technology. This advance has provided enormous opportunities to improve plant resistance to pests, diseases and herbicides, and to modify biosynthetic processes to change the quality of plant products. However, the availability of an efficient transformation method to introduce foreign DNA remains to be a substantial barrier for most monocot species, including maize.

There have been many methods attempted for the transformation of monocotyledonous plants, wherein "biolistics" is the most widely used transformation method. In the "biolistics" (microprojectile-mediated DNA delivery) method microprojectile particles are coated with DNA and accelerated by a mechanical device to a speed high enough to penetrate the plant cell wall and nucleus (WO 91/02071). The foreign DNA gets incorporated into the host DNA and results in a transformed cell. There are many variations on the "biolistics" method (Sanford 1990; Fromm 1990; Christou 1988; Sautter 1991). The method has been used to produce stably transformed monocotyledonous plants including rice and maize (Christou 1991; Gordon-Kamm 1990; Vasil 1992, 1993; Wan 1994; Sommers 1992). However, even with the more recent improvements it still requires 4 to 6 months to recover transgenic plants (Weeks 1993; Vasil 1992, 1993; Becker 1994, Rasco-Gaunt 2001). Microprojectile-mediated DNA delivery brings about a number of problems such as frequent fragmentation of the DNA prior to its integration, random integration in transcribed as well as non-transcribed chromosomal regions, predominantly multiple insertion of the sequence to be transferred, complex integration patterns, integration of backbone sequences including selectable marker genes at the same locus. Moreover, microprojectile-mediated plant transformation is generally based upon genotype-dependent cell culture methods which often require a secondary transfer of the transgene into the background of elite breeding material via long-lasting back-crossing.

Protoplast based methods have been used mostly in rice, where DNA is delivered to the protoplasts through liposomes, PEG, or electroporation (Shimamoto 1989; Datta 1990b). Protoplasts may be isolated from various tissues but require in general the use of cell wall-degrading enzymes. It is considered likely that the use of cell wall-degrading enzymes can inhibit the subsequent regeneration process. Furthermore, most protoplast based methods require the establishment of long-term embryogenic suspension cultures. Some regenerants from protoplasts are infertile and phenotypically abnormal due to somaclonal variation during the long-term suspension culture (Davey 1991; Rhodes 1988). Transformation by electroporation involves the application of short, high-voltage electric fields to create "pores" in the cell membrane through which DNA is taken-up. This method has been used to produce stably transformed monocotyledonous plants (Paszkowski 1984; Shillito 1985; Fromm 1986) especially from rice (Shimamoto 1989; Datta 1990b; Hayakawa 1992).

A number of other methods have been reported for the transformation of monocotyledonous plants including, for example, the "pollen tube method" (WO 93/18168; Luo 1988), macro-injection of DNA into floral tillers (Du 1989; De la Pena 1987), injection of *Agrobacterium* into developing caryopses (WO 00/63398), and tissue incubation of seeds in DNA solutions (Töpfer 1989). Direct injection of exogenous DNA into the fertilized plant ovule at the onset of embryogenesis was disclosed in WO 94/00583.

While widely useful in dicotyledonous plants, *Agrobacterium*-mediated gene transfer has long been disappointing when adapted to use in monocots. There are several reports in the literature claiming *Agrobacterium* transformation of monocotyledons (e.g., discussed WO 94/00977). These are specifically the methods of Gould 1991; Mooney 1991; and Raineri 1990, which claim *Agrobacterium* transformation of maize, rice and wheat. There is some evidence of gene transfer in these methods but they lack convincing evidence for transfer efficiency, reproducibility, and confirmation of gene transfer (Potrykus 1990), and lack of evidence of the transgene inheritance in the progeny when plants are produced. In the work of Gould where evidence of transformed plants was presented there was no Mendelian inheritance of the genes. Attempts by Hiei et al. (1994) suggested that transgenic rice plants could be obtained following *Agrobacterium*-mediated transformation, but the particular bacterial strains used and the choice of bacterial vectors were critical for successfully obtaining transgenics. A paper by Ishida et al. (1996) indicated that high-efficiency transformation of maize was possible by co-culture of immature embryos with *A. tumefaciens*. In both reports on rice and maize transformation, a superbinary vector pTOK233 containing additional copies of the virB, virC and virG genes was used to achieve high-efficiency transformation. WO 95/06722 and EP-A1 672 752 disclose a method of transforming monocotyledons using scutellum of immature embryos with *A. tumefaciens*, which immature embryo has not been subjected to a dedifferentiation treatment. EP-A1 0 709 462 describes a method for transforming monocotyledonous plants, wherein the improvement is pointed out to include a recovery period after the co-cultivation step without a selection device for one day.

Although the methods known in the art, especially those provided in WO 95/06722, provide means for producing transgenic *Zea mays* plants, all these methods are still time and labor intensive. Especially when large numbers of transgenic plants need to be established (such as for example in a genomics based screening approach requiring construction of hundreds to thousands of different transgenic plants) efficiency is of high commercial importance.

Accordingly, the object of the present invention is to provide an improved, efficient method for transforming *Zea mays* plants, with which the time required for obtaining regenerated plants from the time of transformation is shorter than that in the conventional methods. This objective is achieved by the present invention.

SUMMARY OF THE INVENTION

Accordingly a first embodiment of the invention is related to a method for generating a transgenic *Zea mays* plant comprising the steps of a. isolating an immature embryo of a *Zea mays* plant, and
b. co-cultivating said isolated immature embryo, which has not been subjected to a dedifferentiation treatment, with a soil-borne bacterium belonging to genus Rhizobiaceae comprising at least one transgenic T-DNA, said T-DNA comprising at least one selectable marker gene, with a co-cultivation medium, and
c. transferring the co-cultivated immature embryos to a recovering medium comprising
   i. an effective amount of at least one antibiotic that inhibits or suppresses the growth of soil-borne bacterium, and
   ii. L-proline in a concentration from about 1 g/l to about 10 g/l, and
   iii. silver nitrate in a concentration from about 1 µM to about 50 µM, and
   iv. an effective amount of at least one auxin compound, but not comprising an effective amount of a phytotoxic selection agent, and
d. inducing formation of embryogenic callus and selecting transgenic callus on a medium comprising,
   i. an effective amount of at least one auxin compound, and
   ii. an effective amount of a selection agent allowing for selection of cells comprising the transgenic T-DNA, and
e. regenerating and selecting plants containing the transgenic T-DNA from the said transgenic callus.

The immature embryo is preferably from the group consisting of inbreds, hybrids, F1 between (preferably different) inbreds, F1 between an inbred and a hybrid, F1 between an inbred and a naturally-pollinated variety, commercial F1 varieties, any F2 crossing or self-pollination between the before mentioned varieties and the progeny of any of the before mentioned.

Preferably, the immature embryo is isolated from a cross of a (HiIIA×A188) hybrid with an inbred-line of which representative seed having been deposited under the Budapest Treaty with the American Type Culture Collection (Manassas, Va. 20110-2209, USA) under the Patent Deposit Designation PTA-6170 (for seeds of line BPS553), and PTA-6171 (for seeds of line BPS631).

In a preferred embodiment the immature embryo is one in the stage of not less than 2 days after pollination. Preferably the immature embryos are directly isolated and prepared in the co-cultivation medium without additional washing steps. Preferably, the immature embryo is subjected to transformation (co-cultivation) without dedifferentiating pretreatment. Treatment of the immature embryos with an enzyme or injuring is optional. Embryos dissected from ears harvested from greenhouse and stored in a fridge at about 4° C. up to 10 days remain to be transformable.

Preferably the soil-borne bacterium is a bacterium belonging to family *Agrobacterium*, more preferably a disarmed *Agrobacterium tumefaciens* or *rhizogenes* strain. In another preferred embodiment the soil-borne bacterium is a disarmed strain variant of *Agrobacterium rhizogenes* strain K599 (NCPPB 2659). Such strains are described in U.S. provisional application Application No. 60/606,789, filed Sep. 2, 2004, hereby incorporated entirely by reference.

In another preferred embodiment for the infection and co-cultivation step a suspension of the soil-borne bacterium (e.g., *Agrobacteria*) in the co-cultivation or infection medium is directly applied to each embryo, and excess amount of liquid covering the embryo is removed. Removal can be done by various means, preferably through either air-drying or absorbing. In a preferred embodiment from about 1 to about 10 µl of a suspension of the soil-borne bacterium (e.g., *Agrobacteria*) are employed. Preferably, the immature embryo is infected with *Agrobacterium* directly on the co-cultivation medium. Preferably, the bacterium is employed in concentration of $10^6$ to $10^{11}$ CFU/ml (cfu: colony forming units).

Preferably, the medium employed during co-cultivation comprises from about 1 µM to about 10 µM of silver nitrate and from about 50 mg/L to about 1,000 mg/L of L-Cysteine.

In a preferred embodiment the selection step is carried out in a single selection step without intermediate tissue transfer.

In another preferred embodiment, the rooted plantlets resulting from the regeneration step are directly transferred into soil medium.

Another preferred embodiment of the invention relates to a maize plant obtained by crossing a (HiIIA×A188) hybrid with an inbred-line selected from the group of which representative seed having been deposited under the Budapest Treaty with the American Type Culture Collection (Manassas, Va. 20110-2209, USA) under the Patent Deposit Designation PTA-6170 (for seeds of line BPS553), and PTA-6171 (for seeds of line BPS631).

Preferably said maize plant is transgenic (e.g., comprises a transgenic T-DNA). Other objects of the invention relate to descendants of said maize plant (such as for example inbred lines), inbreds or hybrid plants produced from said descendants, and parts of the before mentioned plants. Such parts may include but are not limited to tissue, cells, pollen, ovule, roots, leaves, seeds, microspores, and vegetative parts.

Another embodiment of the invention relates to a method for subsequent transformation of at least two DNA constructs into a plant comprising the steps of:
a) a first transformation with a first construct said construct comprising a first mutated ahas selection marker gene, said first gene conferring resistance to imazethapyr but sensitive to imazaquin, and selecting plants resistant to imazethapyr, and
b) a second transformation with a second construct said construct comprising a second mutated ahas selection marker gene, said second gene conferring resistance to both imazethapyr and imazaquin, and selecting plants resistant to imazaquin.

Preferably, said first gene is an XI12 ahas mutant gene and/or wherein said second gene is an XA17 ahas mutant gene. More preferably, said plant is a *Zea mays* plant.

Another embodiment of the invention relates to a plant cell or plant comprising a
a) a first mutated ahas selection marker gene, said first gene conferring resistance to imazethapyr but sensitive to imazaquin, and
b) a second mutated ahas selection marker gene, said second gene conferring resistance to both imazethapyr and imazaquin.

Preferably, said first gene is an XI12 ahas mutant gene and/or wherein said second gene is an XA17 ahas mutant gene. More preferably, said first and said second gene are transgenes. The plant is preferably a *Zea mays* plant.

GENERAL DEFINITIONS

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

As used herein, the word "or" means any one member of a particular list and also includes any combination of members of that list.

The term "nucleic acid" refers to deoxyribonucleotides or ribonucleotides and polymers or hybrids thereof in either single-or double-stranded, sense or antisense form.

Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used interchangeably herein with "gene", "cDNA, "mRNA", "oligonucleotide," and "polynucleotide".

The phrase "nucleic acid sequence" as used herein refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid which is transcribed and translated in a sequence-specific manner to produce into a particular polypeptide or protein when placed under the control of appropriate regulatory sequences. The coding region is said to encode such a polypeptide or protein.

The term "antisense" is understood to mean a nucleic acid having a sequence complementary to a target sequence, for example a messenger RNA (mRNA) sequence the blocking of whose expression is sought to be initiated by hybridization with the target sequence.

The term "sense" is understood to mean a nucleic acid having a sequence which is homologous or identical to a target sequence, for example a sequence which binds to a protein transcription factor and which is involved in the expression of a given gene. According to a preferred embodiment, the nucleic acid comprises a gene of interest and elements allowing the expression of the said gene of interest.

The term "gene" refers to a coding region operably joined to appropriate regulatory sequences capable of regulating the expression of the polypeptide in some manner. A gene includes untranslated regulatory regions of DNA (e.g., promoters, enhancers, repressors, etc.) preceding (upstream) and following (downstream) the coding region (open reading frame, ORF) as well as, where applicable, intervening sequences (i.e., introns) between individual coding regions (i.e., exons).

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine and on the 3'-side by one of the three triplets which specify stop codons (i.e., TAA, TAG, TGA). In addition to containing introns, genomic forms of a gene may also include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

The terms "polypeptide", "peptide", "oligopeptide", "polypeptide", "gene product", "expression product" and "protein" are used interchangeably herein to refer to a polymer or oligomer of consecutive amino acid residues.

The term "isolated" as used herein means that a material has been removed from its original environment. For example, a naturally-occurring polynucleotide or polypeptide present in a living animal is not isolated, but the same polynucleotide or polypeptide, separated from some or all of the coexisting materials in the natural system, is isolated. Such polynucleotides can be part of a vector and/or such polynucleotides or polypeptides could be part of a composition, and would be isolated in that such a vector or composition is not part of its original environment.

The term "wild-type", "natural" or of "natural origin" means with respect to an organism, polypeptide, or nucleic acid sequence, that said organism is naturally occurring or available in at least one naturally occurring organism which is not changed, mutated, or otherwise manipulated by man.

The term "transgenic" or "recombinant" as used herein (e.g., with regard to a *Zea mays* plant or plant cell) is intended to refer to cells and/or plants that have incorporated exogenous genes or DNA sequences, including but not limited to genes or DNA sequences which are perhaps not normally present, genes not normally transcribed and translated ("expressed") in a given cell type, or any other genes or DNA sequences which one desires to introduce into the non-transformed cell and/or plant, such as genes which may normally be present in the non-transformed cell and/or plant but which one desires to have altered expression.

Preferably, the terms "transgenic" or "recombinant" with respect to, for example, a nucleic acid sequence (or an organism, expression cassette or vector comprising said nucleic acid sequence) refers to all those constructs originating by recombinant methods in which either a) said nucleic acid sequence, or b) a genetic control sequence linked operably to said nucleic acid sequence a), for example a promoter, or c) (a) and (b)

is not located in its natural genetic environment or has been modified by recombinant methods, an example of a modification being a substitution, addition, deletion, inversion or insertion of one or more nucleotide residues. Natural genetic environment refers to the natural chromosomal locus in the organism of origin, or to the presence in a genomic library. In the case of a genomic library, the natural genetic environment of the nucleic acid sequence is preferably retained, at least in part. The environment flanks the nucleic acid sequence at least at one side and has a sequence of at least 50 bp, preferably at least 500 bp, especially preferably at least 1000 bp, very especially preferably at least 5000 bp, in length. A naturally occurring expression cassette—for example the naturally occurring combination of a promoter with the corresponding gene—becomes a recombinant expression cassette when it is modified by non-natural, synthetic "artificial" methods such as, for example, mutagenization. Such methods have been described (U.S. Pat. No. 5,565,350; WO 00/15815). Preferably, the term "recombinant" with respect to nucleic acids as used herein means that the nucleic acid is covalently joined and adjacent to a nucleic acid to which it is not adjacent in its natural environment. "Recombinant" polypeptides or proteins refer to polypeptides or proteins produced by recombinant DNA techniques, i.e., produced from cells transformed by an exogenous recombinant DNA construct encoding the desired polypeptide or protein. Recombinant nucleic acids and polypeptide may also comprise molecules which as such does not exist in nature but are modified, changed, mutated or otherwise manipulated by man.

A "recombinant polypeptide" is a non-naturally occurring polypeptide that differs in sequence from a naturally occurring polypeptide by at least one amino acid residue. Preferred methods for producing said recombinant polypeptide and/or nucleic acid may comprise directed or non-directed mutagenesis, DNA shuffling or other methods of recursive recombination.

The terms "heterologous nucleic acid sequence" or "heterologous DNA" are used interchangeably to refer to a nucleotide sequence which is ligated to a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is expressed.

The "efficiency of transformation" or "frequency of transformation" as used herein can be measured by the number of transformed cells (or transgenic organisms grown from individual transformed cells) that are recovered under standard experimental conditions (i.e. standardized or normalized with respect to amount of cells contacted with foreign DNA, amount of delivered DNA, type and conditions of DNA delivery, general culture conditions etc.) For example, when isolated immature embryos are used as starting material for transformation, the frequency of transformation can be expressed as the number of transgenic plant lines obtained per 100 isolated immature embryos transformed.

The term "cell" refers to a single cell. The term "cells" refers to a population of cells. The population may be a pure population comprising one cell type. Likewise, the population may comprise more than one cell type. In the present invention, there is no limit on the number of cell types that a cell population may comprise. The cells may be synchronize or not synchronized, preferably the cells are synchronized.

The term "chromosomal DNA" or "chromosomal DNA-sequence" is to be understood as the genomic DNA of the cellular nucleus independent from the cell cycle status. Chromosomal DNA might therefore be organized in chromosomes or chromatics, they might be condensed or uncoiled. An insertion into the chromosomal DNA can be demonstrated and analyzed by various methods known in the art like e.g., PCR analysis, Southern blot analysis, fluorescence in situ hybridization (FISH), and in situ PCR.

The term "structural gene" as used herein is intended to mean a DNA sequence that is transcribed into mRNA which is then translated into a sequence of amino acids characteristic of a specific polypeptide.

The term "expression" refers to the biosynthesis of a gene product. For example, in the case of a structural gene, expression involves transcription of the structural gene into mRNA and—optionally—the subsequent translation of mRNA into one or more polypeptides.

The term "transformation" includes introduction of genetic material into plant cells, preferably resulting in chromosomal integration and stable heritability through meiosis. Transformation also includes introduction of genetic material into plant cells in the form of plant viral vectors involving epichromosomal replication and gene expression which may exhibit variable properties with respect to meiotic stability.

The term "expression cassette" or "expression construct" as used herein is intended to mean the combination of any nucleic acid sequence to be expressed in operable linkage with a promoter sequence and—optionally—additional elements (like e.g., terminator and/or polyadenylation sequences) which facilitate expression of said nucleic acid sequence.

The term "promoter" as used herein is intended to mean a DNA sequence that directs the transcription of a DNA sequence (e.g., a structural gene). Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter. Also, the promoter may be regulated in a tissue-specific or tissue preferred manner such that it is only active in transcribing the associated coding region in a specific tissue type(s) such as leaves, roots or meristem.

The term "operable linkage" or "operably linked" is to be understood as meaning, for example, the sequential arrangement of a regulatory element (e.g. a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of said nucleic acid sequence. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly is preferably less than 200 base pairs, especially preferably less than 100 base pairs, very especially preferably less than 50 base pairs. Operable linkage, and an expression cassette, can be generated by means of customary recombination and cloning techniques as described (e.g., in Maniatis 1989; Silhavy 1984; Ausubel 1987; Gelvin 1990). However, further sequences which, for example, act as a linker with specific cleavage sites for restriction enzymes, or as a signal peptide, may also be positioned between the two sequences. The insertion of sequences may also lead to the expression of fusion proteins. Preferably, the expression cassette, consisting of a linkage of promoter and nucleic acid sequence to be expressed, can exist in a vector-integrated form and be inserted into a plant genome, for example by transformation.

DETAILED DESCRIPTION OF THE INVENTION

A first embodiment of the invention relates to a method for generating a transgenic *Zea mays* plant comprising the steps of
a. isolating an immature embryo of a *Zea mays* plant, and
b. co-cultivating said isolated immature embryo, which has not been subjected to a dedifferentiation treatment, with a soil-borne bacterium belonging to genus Rhizobiaceae comprising at least one transgenic T-DNA, said T-DNA comprising at least one selectable marker gene, with a co-cultivation medium, and
c. transferring the co-cultivated immature embryos to a recovering medium comprising
  i. an effective amount of at least one antibiotic that inhibits or suppresses the growth of soil-borne bacterium, and
  ii. L-proline in a concentration from about 1 g/l to about 10 g/l, and
  iii. silver nitrate in a concentration from about 1 µM to about 50 µM, and
  iv. an effective amount of at least one auxin compound, but not comprising an effective amount of a phytotoxic selection agent, and
d. inducing formation of embryogenic callus and selecting transgenic callus on a medium comprising,
  i. an effective amount of at least one auxin compound, and
  ii. an effective amount of a selection agent allowing for selection of cells comprising the transgenic, and
e. regenerating and selecting plants containing the transgenic T-DNA from the said transgenic callus.

1. Source and Preparation of the Immature Embryo

The immature embryo can be isolated from virtually any *Zea mays* variety or plant.

The immature embryo is preferably from the group consisting of inbreds, hybrids, F1 between (preferably different) inbreds, F1 between an inbred and a hybrid, F1 between an inbred and a naturally-pollinated variety, commercial F1 varieties, any F2 crossing or self-pollination between the before mentioned varieties and the progeny of any of the before mentioned.

All combinations of male and female parents for the before mentioned lines and crossings are included. Suitable *Zea mays* varieties include but are not limited to P3732, A188, H84, B37Ht, Mo117Ht, W117Ht, Oh43, H99, W64A Ht rhm, F1 (A188×Black Mexican Sweet), F1 (A188×B73Ht), F1 (B73Ht×A188), F1 (H84×A188), F1 (Mo17Ht×A188) and F1 (C103×A188). Such varieties are available as seeds from deposits such as American Type Culture Collection (ATCC) and other deposits for seed material known in the art.

More preferably, the immature embryo is isolated from a cross of a F1 or F2 (HiIIA×A188) plants with an inbred-line.

F1 seeds of corn genotype HiIIA×A188 can be preferably produced by crossing HiIIA (female parent) with inbred line A188 (male), and planted in the greenhouse as pollen donor. F2 seeds of (HiIIA×A188) are produced by self-pollination of F1 (HiIIA×A188) plants either in the greenhouse or in the field, and planted in the greenhouse as the pollen donor.

Most preferred as inbred lines for the crossing with a F1 or F2 (HiIIA×A188) plants are lines selected from group of lines selected from the group of which representative seed having been deposited under the Budapest Treaty with the American Type Culture Collection (Manassas, Va. 20110-2209, USA) under the Patent Deposit Designation PTA-6170 (for seeds of line BPS553), and PTA-6171 (for seeds of line BPS631).

Hybrid immature embryos of BPS553×(HiIIA×A188) or BPS631×(HiIIA×A188) are preferably produced using inbred line BPS553 or BPS631 as the female parents, and either F1 or F2 (HiIIA×A188) plants as the male parent in the greenhouse. These hybrid immature embryos have demonstrated extraordinary high transformability in comparison with (HiIIA×A188) immature embryos alone, known in the art as one of the best transformable *Zea mays* material (Ishida et al. 1996, Frame et al. 2002). The transformability of a hybrid immature embryo from a cross between a (HiIIA×A188) hybrid the BPS553 lines is at least twice the efficiency as for a (HiIIA×A188) embryo (for a comparison see Example 7 below). In consequence the above mentioned crosses are superior material for *Zea mays* transformation.

Accordingly, another preferred embodiment of the invention relates to a maize plant obtained by crossing a (HiIIA×A188) hybrid with an inbred-line selected from the group of which representative seed having been deposited under the Budapest Treaty with the American Type Culture Collection (Manassas, Va. 20110-2209, USA) under the Patent Deposit Designation PTA-6170 (for seeds of line BPS553), and PTA-6171 (for seeds of line BPS631). Preferably said maize plant is transgenic (e.g., comprises a transgenic T-DNA). Other objects of the invention relate to descendants of said maize plant (such as for example inbred lines), inbreds or hybrid plants produced from said descendants, and parts of the before mentioned plants. Such parts may include but are not limited to tissue, cells, pollen, ovule, roots, leaves, seeds, microspores, and vegetative parts.

*Zea mays* plants for isolation of immature embryos are grown and pollinated as known in the art, preferably as described below in the examples.

The term "immature embryo" as used herein means the embryo of an immature seed which is in the stage of early development and maturation after pollination. The developmental stage of the immature embryos to be treated by the method of the present invention are not restricted and the collected embryos may be in any stage after pollination. Preferred embryos are those collected on not less than 2 days after their fertilization. Also preferred are scutella of immature embryos capable of inducing dedifferentiated calli having an ability to regenerate normal plants after having been transformed by the method mentioned below.

In a preferred embodiment the immature embryo is one in the stage of not less than 2 days after pollination. More preferably, immature embryos are isolated from ears from corn plants (preferably the first ear that comes out) harvested 7 to 14 days (preferably 8 to 11 days) after pollination (DAP). Exact timing of harvest varies depending on growth conditions and maize variety. The size of immature embryos is a good indication of their stage of development. The optimal length of immature embryos for transformation is about 1 to 1.6 mm, including the length of the scutellum. The embryo should be translucent, not opaque.

In a preferred embodiment of the invention, the immature embryos are isolated and directly placed on the surface a solidified co-cultivation medium without additional washing steps. While the methods described in the art all include several preparation and washing steps all these are omitted in said improvement saving significant time and costs. With the present invention, the *Agrobacterium* infection step takes place on the co-cultivation medium, instead of in a tube containing *Agrobacterium* suspension cells, known to the art.

Preferably, the immature embryo is subjected to transformation (co-cultivation) without dedifferentiating pretreatment. Treatment of the immature embryos with a cell wall degrading enzyme or injuring (e.g., cutting with scalpels or perforation with needles) is optional. However, this degradation or injury step is not necessary and is omitted in a preferred embodiment of the invention.

The term "dedifferentiation", "dedifferentiation treatment" or "dedifferentiation pretreatment" means a process of obtaining cell clusters, such as callus, that show unorganized growth by culturing differentiated cells of plant tissues on a dedifferentiation medium. More specifically, the term "dedifferentiation" as used herein is intended to mean the process of formation of rapidly dividing cells without particular function in the scope of the plant body. These cells often possess an increased potency with regard to its ability to develop into various plant tissues. Preferably the term is intended to mean the reversion of a differentiated or specialized tissues to a more pluripotent or totipotent (e.g., embryonic) form. Dedifferentiation may lead to reprogramming of a plant tissue (revert first to undifferentiated, non-specialized cells. then to new and different paths). The term "totipotency" as used herein is intended to mean a plant cell containing all the genetic and/or cellular information required to form an entire plant. Dedifferentiation can be initiated by certain plant growth regulators (e.g., auxin and/or cytokinin compounds), especially by certain combinations and/or concentrations thereof.

2. Co-cultivation

The soil-borne bacterium employed for transfer of a T-DNA into the immature embryo can be any specie of the Rhizobiaceae family. The Rhizobiaceae family comprises the genera *Agrobacterium, Rhizobium, Sinorhizobium*, and *Allorhizobium* are genera within the bacterial family and has been included in the alpha-2 subclass of Proteobacteria on the basis of ribosomal characteristics. Members of this family are aerobic, Gram-negative. The cells are normally rod-shaped (0.6-1.0 µm by 1.5-3.0 µm), occur singly or in pairs, without endospore, and are motile by one to six peritrichous flagella. Considerable extracellular polysaccharide slime is usually produced during growth on carbohydrate-containing media. Especially preferred are Rhizobiaceae such as *Sinorhizobium meliloti, Sinorhizobium medicae, Sinorhizobium fredii, Rhizobium* sp. NGR234, *Rhizobium* sp. BR816, *Rhizobium* sp. N33, *Rhizobium* sp. GRH2, *Sinorhizobium saheli, Sinorhizobium terangae, Rhizobium leguminosarum biovar trifolii, Rhizobium leguminosarum biovar viciae, Rhizobium leguminosarum biovar phaseoli, Rhizobium tropici, Rhizobium etli, Rhizobium galegae, Rhizobium galicum, Rhizobium giardinii, Rhizobium hainanense, Rhizobium mongolense, Rhizobium lupini, Mesorhizobium loti, Mesorhizobium huakuii, Mesorhizobium ciceri, Mesorhizobium mediterraneium, Mesorhizobium tianshanense, Bradyrhizobium elkanni, Bradyrhizobium japonicum, Bradyrhizobium liaoningense, Azorhizobium caulinodans, Allobacterium undicola, Phyllobacterium myrsinacearum, Agrobacterium tumefaciens, Agrobacterium radiobacter, Agrobacterium rhizogenes, Agrobacterium vitis*, and *Agrobacterium rubi*.

The monophyletic nature of *Agrobacterium, Allorhizobium* and *Rhizobium* and their common phenotypic generic circumscription support their amalgamation into a single genus, *Rhizobium*. The classification and characterization of *Agrobacterium* strains including differentiation of *Agrobacterium tumefaciens* and *Agrobacterium rhizogenes* and their various opine-type classes is a practice well known in the art (see for example Laboratory guide for identification of plant pathogenic bacteria, 3rd edition. (2001) Schaad, Jones, and Chun (eds.) ISBN 0890542635; for example the article of Moore et al. published therein). Recent analyses demonstrate that classification by its plant-pathogenic properties may not be justified. Accordingly more advanced methods based on genome analysis and comparison (such as 16S rRNA sequencing; RFLP, Rep-PCR, etc.) are employed to elucidate the relationship of the various strains (see for example Young 2003, Farrand 2003, de Bruijn 1996, Vinuesa 1998). The phylogenetic relationships of members of the genus *Agrobacterium* by two methods demonstrating the relationship of *Agrobacterium* strains K599 are presented in Llob 2003 (FIG. 2).

It is known in the art that not only *Agrobacterium* but also other soil-borne bacteria are capable to mediate T-DNA transfer provided that they the relevant functional elements for the T-DNA transfer of a Ti- or Ri-plasmid (Klein & Klein 1953; Hooykaas 1977; van Veen 1988).

Preferably, the soil-born bacterium is of the genus *Agrobacterium*. The term "*Agrobacterium*" as used herein refers to a soil-borne, Gram-negative, rod-shaped phytopathogenic bacterium. The species of *Agrobacterium, Agrobacterium tumefaciens* (syn. *Agrobacterium radiobacter*), *Agrobacterium rhizogenes, Agrobacterium rubi* and *Agrobacterium vitis*, together with *Allorhizobium undicola*, form a monophyletic group with all *Rhizobium* species, based on comparative 16S rDNA analyses (Sawada 1993, Young 2003). *Agrobacterium* is an artificial genus comprising plant-pathogenic species.

The term Ti-plasmid as used herein is referring to a plasmid which is replicable in *Agrobacterium* and is in its natural, "armed" form mediating crown gall in *Agrobacterium* infected plants. Infection of a plant cell with a natural, "armed" form of a Ti-plasmid of *Agrobacterium* generally results in the production of opines (e.g., nopaline, agropine, octopine etc.) by the infected cell. Thus, *Agrobacterium* strains which cause production of nopaline (e.g., strain LBA4301, C58, A208) are referred to as "nopaline-type" *Agrobacteria; Agrobacterium* strains which cause production of octopine (e.g., strain LBA4404, Ach5, B6) are referred to as "octopine-type" *Agrobacteria*; and *Agrobacterium* strains which cause production of agropine (e.g., strain EHA105, EHA101, A281) are referred to as "agropine-type" Agrobacteria. A disarmed Ti-plasmid is understood as a Ti-plasmid lacking its crown gall mediating properties but otherwise providing the functions for plant infection. Preferably, the T-DNA region of said "disarmed" plasmid was modified in a way, that beside the border sequences no functional internal Ti-sequences can be transferred into the plant genome. In a preferred embodiment—when used with a binary vector system—the entire T-DNA region (including the T-DNA borders) is deleted.

The term Ri-plasmid as used herein is referring to a plasmid which is replicable in *Agrobacterium* and is in its natural, "armed" form mediating hairy-root disease in *Agrobacterium* infected plants. Infection of a plant cell with a natural, "armed" form of an Ri-plasmid of *Agrobacterium* generally results in the production of opines (specific amino sugar derivatives produced in transformed plant cells such as e.g., agropine, cucumopine, octopine, mikimopine etc.) by the infected cell. *Agrobacterium rhizogenes* strains are traditionally distinguished into subclasses in the same way *A. tumefaciens* strains are. The most common strains are agropine-type strains (e.g., characterized by the Ri-plasmid pRi-A4), mannopine-type strains (e.g., characterized by the Ri-plasmid pRi8196) and cucumopine-type strains (e.g., characterized by the Ri-plasmid pRi2659). Some other strains are of the mikimopine-type (e.g., characterized by the Ri-plasmid pRi1723). Mikimopine and cucumopine are stereo isomers but no homology was found between the pRi plasmids on the nucleotide level (Suzuki 2001). A disarmed Ri-plasmid is understood as a Ri-plasmid lacking its hairy-root disease mediating proper-ties but otherwise providing the functions for plant infection. Preferably, the T-DNA region of said "disarmed" Ri plasmid was modified in a way, that beside the border sequences no functional internal Ri-sequences can be transferred into the plant genome. In a preferred embodiment—when used with a binary vector system—the entire T-DNA region (including the T-DNA borders) is deleted.

The Ti and Ri plasmids of *A. tumefaciens* and *A. rhizogenes*, respectively, carry genes responsible for genetic transformation of the plant (Kado 1991). Vectors are based on the *Agrobacterium* Ti- or Ri-plasmid and utilize a natural system of DNA transfer into the plant genome. As part of this highly developed parasitism *Agrobacterium* transfers a defined part of its genomic information (the T-DNA; flanked by about 25 bp repeats, named left and right border) into the chromosomal DNA of the plant cell (Zupan 2000). By combined action of the so called vir genes (part of the original Ti-plasmids) said DNA-transfer is mediated. For utilization of this natural system, Ti-plasmids were developed which lack the original tumor inducing genes ("disarmed vectors"). In a further improvement, the so called "binary vector systems", the T-DNA was physically separated from the other functional elements of the Ti-plasmid (e.g., the vir genes), by being incorporated into a shuttle vector, which allowed easier handling (EP-A 120 516; U.S. Pat. No. 4,940,838). These binary vectors comprise (beside the disarmed T-DNA with its border sequences), prokaryotic sequences for replication both in *Agrobacterium* and *E. coli*. It is an advantage of *Agrobacterium*-mediated transformation that in general only the DNA flanked by the borders is transferred into the genome and that preferentially only one copy is inserted. Descriptions of *Agrobacterium* vector systems and methods for *Agrobacterium*-mediated gene transfer are known in the art (Miki 1993; Gruber 1993; Moloney 1989).

Hence, for *Agrobacteria*-mediated transformation the genetic composition (e.g., comprising an expression cassette) is integrated into specific plasmids, either into a shuttle or intermediate vector, or into a binary vector. If a Ti or Ri plasmid is to be used for the transformation, at least the right border, but in most cases the right and left border, of the Ti or Ri plasmid T-DNA is linked to the expression cassette to be introduced in the form of a flanking region. Binary vectors are preferably used. Binary vectors are capable of replication both in *E. coli* and in *Agrobacterium*. They may comprise a selection marker gene and a linker or polylinker (for insertion of e.g. the expression cassette to be transferred) flanked by the right and left T-DNA border sequence. They can be transferred directly into *Agrobacterium* (Holsters 1978). The selection marker gene permits the selection of transformed Agrobacteria and is, for example, the nptII gene, which confers resistance to kanamycin. The *Agrobacterium* which acts as host organism in this case should already contain a plasmid with the vir region. The latter is required for transferring the T-DNA to the plant cell. An *Agrobacterium* transformed in this way can be used for transforming plant cells. The use of T-DNA for transforming plant cells has been studied and described intensively (EP 120 516; Hoekema 1985; An 1985).

Common binary vectors are based on "broad host range"-plasmids like pRK252 (Bevan 1984) or pTJS75 (Watson 1985) derived from the P-type plasmid RK2. Most of these vectors are derivatives of pBIN19 (Bevan 1984). Various binary vectors are known, some of which are commercially available such as, for example, pBI101.2 or pBIN19 (Clontech Laboratories, Inc. USA). Additional vectors were improved with regard to size and handling (e.g. pPZP; Hajdukiewicz 1994). Improved vector systems are described also in WO 02/00900.

Preferably the soil-borne bacterium is a bacterium belonging to family *Agrobacterium*, more preferably a disarmed *Agrobacterium tumefaciens* or *rhizogenes* strain. In a preferred embodiment, *Agrobacterium* strains for use in the practice of the invention include octopine strains, e.g., LBA4404 or agropine strains, e.g., EHA101 or EHA105. Suitable strains of *A. tumefaciens* for DNA transfer are for example EHA101pEHA101 (Hood 1986), EHA105 [pEHA105] (Li 1992), LBA4404[pAL4404] (Hoekema 1983), C58C1[pMP90] (Koncz & Schell 1986), and C58C1 [pGV2260] (Deblaere 1985). Other suitable strains are *Agrobacterium tumefaciens* C58, a nopaline strain. Other suitable strains are *A. tumefaciens* C58C1 (Van Larebeke 1974), A136 (Watson 1975) or LBA4011 (Klapwijk 1980). In another preferred embodiment the soil-borne bacterium is a disarmed strain variant of *Agrobacterium rhizogenes* strain K599 (NCPPB 2659). Such strains are described in U.S. provisional application Application No. 60/606,789, filed Sep. 2, 2004, hereby incorporated entirely by reference.

Preferably, these strains are comprising a disarmed plasmid variant of a Ti- or Ri-plasmid providing the functions required for T-DNA transfer into plant cells (e.g., the vir genes). In a preferred embodiment, the *Agrobacterium* strain used to transform the plant tissue pre-cultured with the plant phenolic compound contains a L,L-succinamopine type Ti-plasmid, preferably disarmed, such as pEHA101. In another preferred embodiment, the *Agrobacterium* strain used to transform the plant tissue pre-cultured with the plant phenolic compound contains an octopine-type Ti-plasmid, preferably disarmed, such as pAL4404. Generally, when using octopine-type Ti-plasmids or helper plasmids, it is preferred that the virF gene be deleted or inactivated (Jarschow 1991).

The method of the invention can also be used in combination with particular *Agrobacterium* strains, to further increase the transformation efficiency, such as *Agrobacterium* strains wherein the vir gene expression and/or induction thereof is altered due to the presence of mutant or chimeric virA or virG genes (e.g. Hansen 1994; Chen and Winans 1991; Scheeren-Groot, 1994). Preferred are further combinations of *Agrobacterium tumefaciens* strain LBA4404 (Hiei 1994) with supervirulent plasmids. These are preferably pTOK246-based vectors (Ishida 1996).

A binary vector or any other vector can be modified by common DNA recombination techniques, multiplied in *E. coli*, and introduced into *Agrobacterium* by e.g., electroporation or other transformation techniques (Mozo 1991).

*Agrobacterium* is grown and used in a manner similar to that described in Ishida (Ishida 1996). The vector comprising *Agrobacterium* strain may, for example, be grown for 3 days on YP medium (5 g/l yeast extract, 10 g/l peptone, 5 g/l NaCl, 15 g/l agar, pH 6.8) supplemented with the appropriate antibiotic (e.g., 50 mg/l spectinomycin). Bacteria are collected with a loop from the solid medium and resuspended. In a preferred embodiment of the invention, *Agrobacterium* cultures are started by use of aliquots frozen at −80° C.

The transformation of the immature embryos by the *Agrobacterium* may be carried out by merely contacting the immature embryos with the *Agrobacterium*. The concentration of *Agrobacterium* used for infection and co-cultivation may need to be varied. For example, a cell suspension of the *Agrobacterium* having a population density of approximately from $10^5$ to $10^{11}$, preferably $10^6$ to $10^{10}$, more preferably about $10^8$ cells or cfu/ml is prepared and the immature embryos are immersed in this suspension for about 3 to 10 minutes. The resulting immature embryos are then cultured on a solid medium for several days together with the *Agrobacterium*.

In another preferred embodiment for the infection and co-cultivation step a suspension of the soil-borne bacterium (e.g., *Agrobacterium*) in the co-cultivation or infection medium is directly applied to each embryo, and excess amount of liquid covering the embryo is removed. Removal can be done by various means, preferably through either air-drying or absorbing. This is saving labor and time and is reducing unintended *Agrobacterium*-mediated damage by excess *Agrobacterium* usage. In a preferred embodiment from about 1 to about 10 μl of a suspension of the soil-borne bacterium (e.g., *Agrobacterium*) are employed. Preferably, the immature embryo is infected with *Agrobacterium* directly on the co-cultivation medium. Preferably, the bacterium is employed in concentration of $10^6$ to $10^{11}$ cfu/ml.

For *Agrobacterium* treatment of isolated immature embryos, the bacteria are resuspended in a plant compatible co-cultivation medium. Supplementation of the co-culture medium with antioxidants (e.g., silver nitrate), phenol-absorbing compounds (like polyvinylpyrrolidone, Perl 1996) or thiol compounds (e.g., dithiothreitol, L-cysteine, Olhoft 2001) which can decrease tissue necrosis due to plant defense responses (like phenolic oxidation) may further improve the efficiency of *Agrobacterium*-mediated transformation. In another preferred embodiment, the co-cultivation medium comprises of at least one thiol compound, preferably selected from the group consisting of sodium thiosulfate, dithiotrietol (DTT) and L-cysteine. Preferably the concentration is between about 1 mM and 10 mM of L-Cysteine, 0.1 mM to 5 mM DTT, and/or 0.1 mM to 5 mM sodium thiosulfate. Preferably, the medium employed during co-cultivation comprises from about 1 μM to about 10 μM of silver nitrate and from about 50 mg/L to about 1,000 mg/L of L-Cysteine. This results in a highly reduced vulnerability of the immature embryo against *Agrobacterium*-mediated damage (such as induced necrosis) and highly improves overall transformation efficiency.

A range of co-cultivation periods from a few hours to 7 days may be employed. The co-cultivation of *Agrobacterium* with the isolated immature embryos is in general carried out for about 12 hours to about five days, preferably about 1 day to about 3 days.

In an improved embodiment of the invention the isolated immature embryos and/or the *Agrobacteria* may be treated with a phenolic compound prior to or during the *Agrobacterium* co-cultivation. "Plant phenolic compounds" or "plant phenolics" suitable within the scope of the invention are those isolated substituted phenolic molecules which are capable to induce a positive chemotactic response, particularly those who are capable to induce increased vir gene expression in a Ti-plasmid containing *Agrobacterium* sp., particularly a Ti-plasmid containing *Agrobacterium tumefaciens*. Methods to measure chemotactic responses towards plant phenolic compounds have been like e.g., described (Ashby 1988) and methods to measure induction of vir gene expression are also well known (Stachel 1985; Bolton 1986). The pre-treatment and/or treatment during *Agrobacterium tumefaciens* co-cultivation has at least two beneficial effects: Induction of the vir genes of Ti plasmids or helper plasmids (Van Wordragen 1992; Jacq 1993; James 1993; Guivarc'h 1993), and enhancement of the competence for incorporation of foreign DNA into the genome of the plant cell.

Preferred plant phenolic compounds are those found in wound exudates of plant cells. One of the best known plant phenolic compounds is acetosyringone, which is present in a number of wounded and intact cells of various plants, albeit in different concentrations. However, acetosyringone (3,5-dimethoxy-4-hydroxyacetophenone) is not the only plant phenolic which can induce the expression of vir genes. Other examples are α-hydroxy-acetosyringone, sinapinic acid (3,5-dimethoxy-4-hydroxycinnamic acid), syringic acid (4-hydroxy-3,5dimethoxybenzoic acid), ferulic acid (4-hydroxy-3-methoxycinnamic acid), catechol (1,2-dihydroxybenzene), p-hydroxybenzoic acid (4-hydroxybenzoic acid), β-resorcylic acid (2,4-dihydroxybenzoic acid), protocatechuic acid (3,4-dihydroxybenzoic acid), pyrrogallic acid (2,3,4-trihydroxybenzoic acid), gallic acid (3,4,5-trihydroxybenzoic acid) and vanillin (3-methoxy-4-hydroxybenzaldehyde), and these phenolic compounds are known or expected to be able to replace acetosyringone in the cultivation media with similar results. As used herein, the mentioned molecules are referred to as plant phenolic compounds.

Plant phenolic compounds can be added to the plant culture medium either alone or in combination with other plant phenolic compounds. A particularly preferred combination of plant phenolic compounds comprises at least acetosyringone and p-hydroxybenzoic acid, but it is expected that other combinations of two, or more, plant phenolic compounds will also act synergistically in enhancing the transformation efficiency.

Moreover, certain compounds, such as osmoprotectants (e.g. L-proline preferably at a concentration of about 700 mg/L or betaine), phytohormes (inter alia NAA), opines, or sugars, act synergistically when added in combination with plant phenolic compounds.

In one embodiment of the invention, it is preferred that the plant phenolic compound, particularly acetosyringone is added to the medium prior to contacting the isolated immature embryos with *Agrobacteria* (for e.g., several hours to one day). The exact period in which the cultured cells are incubated in the medium containing the plant phenolic compound such as acetosyringone, is believed not to be critical and only limited by the time the immature embryos start to differentiate.

The concentration of the plant phenolic compound in the medium is also believed to have an effect on the development of competence for integrative transformation. The optimal concentration range of plant phenolic compounds in the medium may vary depending on the *Zea mays* variety from which the immature embryos derived, but it is expected that about 100 μM to 700 μM is a suitable concentration for many purposes. However, concentrations as low as approximately 25 μM can be used to obtain a good effect on transformation efficiency. Likewise, it is expected that higher concentrations up to approximately 1000 μM will yield similar effects. Comparable concentrations apply to other plant phenolic compounds, and optimal concentrations can be established easily by experimentation in accordance with this invention.

*Agrobacteria* to be co-cultivated with the isolated immature embryos can be either pre-incubated with acetosyringone or another plant phenolic compound, as known by the person skilled in the art, or used directly after isolation from their culture medium. Particularly suited induction conditions for *Agrobacterium tumefaciens* have been described by Vernade et al. (1988). Efficiency of transformation with *Agrobacterium* can be enhanced by numerous other methods known in the art like for example vacuum infiltration (WO 00/58484), heat shock and/or centrifugation, addition of silver nitrate, sonication etc.

It has been observed within this invention that transformation efficacy of the isolated immature embryos by *Agrobacterium* can be significantly improved by keeping the pH of the co-cultivation medium in a range from 5.4 to 6.4, preferably 5.6 to 6.2, especially preferably 5.8 to 6.0. In an improved embodiment of the invention stabilization of the pH in this range is mediated by a combination of MES and potassium hydrogenphosphate buffers.

3. Recovery and Selection

After the co-cultivation with the bacteria described above remaining bacteria may be removed (e.g., by a washing step). The medium employed after the co-cultivation step preferably contains a bacteriocide (antibiotic). This step is intended to promote initiation of embryogenic callus formation in the *Agrobacterium*-infected embryo, and kill the remaining *Agrobacterium* cells. Accordingly, the method of the invention comprises the step of transferring the co-cultivated immature embryos to a recovering medium comprising i. an effective amount of at least one antibiotic that inhibits or suppresses the growth of the soil-borne bacteria, and
ii. L-proline in a concentration from about 1 g/l to about 10 g/l, and
iii. silver nitrate in a concentration from about 1 µM to about 50 µM, and
iv. an effective amount of at least one auxin compound, but not comprising an effective amount of a phytotoxic selection agent.

Optionally said recovering medium may also comprise at least one plant growth factor. Preferred bactericidal antibiotics to be employed are e.g., carbenicillin (500 mg/L) or Timentin™ (GlaxoSmithKline; a mixture of ticarcillin disodium and clavulanate potassium; 0.8 g Timentin™ contains 50 mg clavulanic acid with 750 mg ticarcillin. Chemically, ticarcillin disodium is N-(2-Carboxy-3,3-dimethyl-7-oxo-4-thia-1-azabicyclo[3.2.0]hept-6-yl)-3-thio-phenemalonamic acid disodium salt. Chemically, clavulanate potassium is potassium (Z)-(2R,5R)-3-(2-hydroxyethylidene)-7-oxo-4-oxa-1-azabicyclo[3.2.0]heptane-2-carboxylate).

It is preferred that during the recovery period no presence of a phytotoxic level of a selection agent (such as a herbicide, phytotoxic antibiotic, phytotoxic D-amino acid etc.) is employed. In case selection of transformed plant cells should be based on use of a negative selection marker (see below) a negative (or phytotoxic) selection agent to be employed in combination with said negative selection marker should be employed only after the recovery period. In contrast agents for positive selection and/or screenable marker selection may be employed even during the recovery period. Examples for preferred recovery media are given below (A-4 or A-5).

The recovery period may last for about 1 day to about 14 days, preferably about 5 days to about 8 days. Preferably, the scutellum side is kept up during this time and do not embedded into the media.

After the recovery step the immature embryos are transferred to and incubated on a selection medium comprising suitable plant growth regulators for induction of embryogenic callus formation. The selection medium further comprises at least one compound which either terminates or at least retard the growth of the non-transformed cells or stimulates growth of transformed cells beyond the growth rate of non-transformed cells.

The term "plant growth regulator" (PGR) as used herein means naturally occurring or synthetic (not naturally occurring) compounds that can regulate plant growth and development. PGRs may act singly or in consort with one another or with other compounds (e.g., sugars, amino acids).

More specifically the medium employed for embryogenic callus induction and selection comprises
i. an effective amount of at least one auxin compound, and
ii. an effective amount of a selection agent allowing for selection of cells comprising the transgenic.

Furthermore the embryogenic callus induction medium may optionally comprise an effective amount of at least one antibiotic that inhibits or suppresses the growth of the soil-borne bacteria (as defined above).

The term "auxin" or "auxin compounds" comprises compounds which stimulate cellular elongation and division, differentiation of vascular tissue, fruit development, formation of adventitious roots, production of ethylene, and—in high concentrations—induce dedifferentiation (callus formation). The most common naturally occurring auxin is indoleacetic acid (IAA), which is transported polarity in roots and stems. Synthetic auxins are used extensively in modern agriculture. Synthetic auxin compounds comprise indole-3-butyric acid (IBA), naphthylacetic acid (NAA), and 2,4-dichlorphenoxyacetic acid (2,4-D).

Preferably, when used as the sole auxin compound, 2,4-D in a concentration of about 0.2 mg/l to about 6 mg/l, more preferably about 0.3 to about 2 mg/l, most preferably about 1.5 mg/l is employed. In case other auxin compounds or combinations thereof are employed, their preferred combinations is chosen in a way that the dedifferentiating effect is equivalent to the effect achieved with the above specified concentrations of 2,4-D when used as the sole auxin compound.

Furthermore, combination of different auxins can be employed, for example a combination of 2,4-D and Picloram. Preferably, 2,4-D in a concentration of about 0.5 mg/l can be combined with one or more other types of auxin compounds e.g. Picloram in a concentration of about 1 to about 2 mg/l for improving quality/quantity of embryogenic callus formation.

The medium may be optionally further supplemented with one or more additional plant growth regulator, like e.g., cytokinin compounds (e.g., 6-benzylaminopurine) and/or other auxin compounds. Such compounds include, but are not limited to, IAA, NAA, IBA, cytokinins, auxins, kinetins, glyphosate, and thiadiazorun. Cytokinin compounds comprise, for example, 6-isopentenyladenine (IPA) and 6-benzoyladenine/6-benzylaminopurine (BAP).

The selection and callus induction period may take from about 1 to about 10 weeks, preferably, 3 to 7 weeks, more preferably 4 to 6 weeks. In between the selection period the callus may be transferred to fresh selection medium one or more times. However alternatively and preferably in an improved, simplified method of the invention, only one selection medium step (without transfer to new selection medium) is required. In consequence, about 30% of time and labor (i.e., 60 min for every 100 immature embryos) is saved. While the basic protocol (with 2 transfer steps) requires growing callus on selection media for usually 5 to 6 weeks, the improved, simplified method requires 4 weeks. Thus, the whole transformation process is shortened by 1 to 2 weeks.

*Agrobacterium*-mediated techniques typically may result in gene delivery into a limited number of cells in the targeted tissue. The insertion of the genetic component into the chromosomal DNA can be demonstrated and analyzed by various methods known in the art like e.g., PCR analysis, Southern blot analysis, fluorescence in situ hybridization (FISH), and in situ PCR. However, selection of successfully transformed from untransformed cells is preferred. Preferably this is done by applying a selection compound which in combination with a selectable marker genes on the T-DNA allows for such selection through a selective advantage. Various selectable markers are known in the art suitable for *Zea mays* transformation. Such markers may include but are not limited to:

i) Negative Selection Markers

Negative selection markers confer a resistance to a biocidal compound such as a metabolic inhibitor (e.g., 2-deoxyglucose-6-phosphate, WO 98/45456), antibiotics (e.g., kanamycin, G 418, bleomycin or hygromycin) or herbicides (e.g., phosphinothricin or glyphosate). Transformed plant material (e.g., cells, tissues or plantlets), which express marker genes, are capable of developing in the presence of concentrations of a corresponding selection compound (e.g., antibiotic or herbicide) which suppresses growth of an untransformed wild type tissue. Especially preferred negative selection markers are those which confer resistance to herbicides. Examples which may be mentioned are:

Phosphinothricin acetyltransferases (PAT; also named Bialophos® resistance; bar; de Block 1987; Vasil 1992, 1993; Weeks 1993; Becker 1994; Nehra 1994; Wan & Lemaux 1994; EP 0 333 033; U.S. Pat. No. 4,975,374)

5-enolpyruvylshikimate-3-phosphate synthase (EPSPS) conferring resistance to Glyphosate® (N-(phosphonomethyl)glycine) (Shah 1986; Della-Cioppa 1987)

Glyphosate® degrading enzymes (Glyphosate® oxidoreductase; gox),

Dalapon® inactivating dehalogenases (deh)

sulfonylurea- and/or imidazolinone-inactivating acetolactate synthases (ahas or ALS; for example mutated ahas/ALS variants with, for example, the S4, XI12, XA17, and/or Hra mutation Bromoxynil® degrading nitrilases (bxn)

Kanamycin- or. geneticin (G418) resistance genes (NPTII; NPTI) coding e.g., for neomycin phosphotransferases (Fraley 1983; Nehra 1994)

2-Desoxyglucose-6-phosphate phosphatase (DOG®1—Gene product; WO 98/45456; EP 0 807 836) conferring resistance against 2-deoxyglucose (Randez-Gil 1995).

hygromycin phosphotransferase (HPT), which mediates resistance to hygromycin (Vanden Elzen 1985).

dihydrofolate reductase (Eichholtz 1987)

Additional negative selectable marker genes of bacterial origin that confer resistance to antibiotics include the aadA gene, which confers resistance to the antibiotic spectinomycin, gentamycin acetyl transferase, streptomycin phosphotransferase (SPT), aminoglycoside-3-adenyl transferase and the bleomycin resistance determinant (Hayford 1988; Jones 1987; Svab 1990; Hille 1986).

Especially preferred are negative selection markers that confer resistance against the toxic effects imposed by D-amino acids like e.g., D-alanine and D-serine (WO 03/060133; Erikson 2004). Especially preferred as negative selection marker in this contest are the daol gene (EC: 1.4.3.3: GenBank Acc.-No.: U60066) from the yeast *Rhodotorula gracilis* (*Rhodosporidium toruloides*) and the *E. coli* gene dsdA (D-serine dehydratase (D-serine deaminase) [EC: 4.3.1.18; GenBank Acc.-No.: J01603).

Transformed plant material (e.g., cells, embryos, tissues or plantlets) which express such marker genes are capable of developing in the presence of concentrations of a corresponding selection compound (e.g., antibiotic or herbicide) which suppresses growth of an untransformed wild type tissue. The resulting plants can be bred and hybridized in the customary fashion. Two or more generations should be grown in order to ensure that the genomic integration is stable and hereditary. Corresponding methods are described (Jenes 1993; Potrykus 1991).

Furthermore, reporter genes can be employed to allow visual screening, which may or may not (depending on the type of reporter gene) require supplementation with a substrate as a selection compound.

Various time schemes can be employed for the various negative selection marker genes. In case of resistance genes (e.g., against herbicides or D-amino acids) selection is preferably applied throughout callus induction phase for about 4 weeks and beyond at least 4 weeks into regeneration. Such a selection scheme can be applied for all selection regimes. It is furthermore possible (although not explicitly preferred) to remain the selection also throughout the entire regeneration scheme including rooting.

For example, with the phosphinothricin resistance gene (bar) as the selective marker, phosphinothricin at a concentration of from about 1 to 50 mg/l may be included in the medium. For example, with the daol gene as the selective marker, D-serine or D-alanine at a concentration of from about 3 to 100 mg/l may be included in the medium. Typical concentrations for selection are 20 to 40 mg/l. For example, with the mutated ahas genes as the selective marker, PURSUIT™ at a concentration of from about 100 to about 1500 nM may be included in the medium. Typical concentrations for selection are about 500 to about 1000 nM.

In a preferred embodiment of the invention the negative selection marker is an ahas genes conferring resistance against sulfonylurea- and/or imidazolinone-type herbicides. In one embodiment of the invention different ahas mutants can be combined in a way to allow multiple subsequent transformation. For example a first transformation can be carried out employing the XI12 mutant ahas2 gene. XI12 mutant maize lines with the mutated ahas2 gene demonstrate to be highly resistant to imazethapyr (PURSUIT™), but sensitive to imazaquin (SCEPTER™) and susceptible to sulfonylurea herbicides. XI12 ahas2 gene isolated from the mutant maize line coupled with selection on imidazolinone herbicide has been used successfully in the art for transformation of corn, rice and wheat (U.S. Pat. No. 6,653,529). In greenhouse study, transgenic rice plants containing the XI12 ahas gene exhibited tolerance to the imidazolinone and sulfonylurea herbicides in a similar fashion as the non-transformed XI12 mutant plant. Similar phenomenon was also observed in a field experiment conducted with transgenic corn plants. Selection for constructs comprising a XI12 mutant ahas selection marker can be carried out for example with PURSUIT™.

The second transformation into the resulting transgenic plant with the XI12 mutant ahas selection marker can be carried out using the XA17 ahas mutant gene. Maize XA17 mutants demonstrates to be highly resistant to both imazethapyr and imazaquin (SCEPTER™), and slightly tolerant to sulfonylurea herbicides. As the maize XA17 gene confers differential tolerance to different imidazolinone compounds and the sulfonylurea herbicides, it can be used as a selectable marker in plant transformation with the choice of using imazethapyr, imazaquin or sulfonylurea as selective reagent.

The mutated XA17 ahas gene and its promoter can be isolated from XA17 mutant line. The sequence was isolated and the gene characterized (Bernasconi 1995). The mutation for XA17 is at nucleotide position 1625 of SEQ ID NO: 2. A single base change from G to T has occurred at this position leading to an amino acid change from Tryptophan to Leucine at amino acid position 542 of SEQ ID NO: 3 (previously referred as 542 mutation in the former naming system). This mutation is equivalent to amino acid position 574 in *Arabidopsis* and now referred as 574 mutation in the new ahas naming system to be consistent for the same mutation in different species.

The XA17 mutant and its phenotype has be described (U.S. Pat. Nos. 4,761,373; 5,304,732; Anderson & Gregeson 1989; Currie 1995; Newhouse 1991). Selection can be carried out with the SCEPTER™ herbicide or sulfonylurea compound for selection. In consequence the combination of the various ahas mutants allows for efficient gene stacking providing a mechanism for double transformation.

Preferably, the XA17 mutant ahas gene is described by a amino acid sequence as described by SEQ ID NO: 3 or a sequence having at least 60%, preferably at least 80%, more preferably at least 90%, most preferably at least 95% homology with the sequence as described by SEQ ID NO 3 and having a Leucine residue at the position corresponding to position 542 of SEQ ID NO: 3 being able to confer resistance against imazethapyr and imazaquin herbicides.

Thus, another embodiment of the invention relates to a method for subsequent transformation of at least two DNA constructs into a plant comprising the steps of:
a) a first transformation with a first construct said construct comprising a first mutated ahas selection marker gene, said first gene conferring resistance to imazethapyr but sensitive to imazaquin, and selecting plants resistant to imazethapyr, and
b) a second transformation with a second construct said construct comprising a second mutated ahas selection marker gene, said second gene conferring resistance to both imazethapyr and imazaquin, and selecting plants resistant to imazaquin.

Preferably, said first gene is an XI12 ahas mutant gene and/or wherein said second gene is an XA17 ahas mutant gene. More preferably, said plant is a Zea mays plant.

Another embodiment of the invention relates to a plant cell or plant comprising a
a) a first mutated ahas selection marker gene, said first gene conferring resistance to imazethapyr but sensitive to imazaquin, and
b) a second mutated ahas selection marker gene, said second gene conferring resistance to both imazethapyr and imazaquin.

Preferably, said first gene is an XI12 ahas mutant gene and/or wherein said second gene is an XA17 ahas mutant gene. More preferably, said first and said second genes are transgenes. The plant is preferably a Zea mays plant.

ii) Positive Selection Marker

Furthermore, positive selection marker can be employed. Genes like isopentenyltransferase from *Agrobacterium tumefaciens* (strain: PO22; Genbank Acc.-No.: AB025109) may—as a key enzyme of the cytokinin biosynthesis—facilitate regeneration of transformed plants (e.g., by selection on cytokinin-free medium). Corresponding selection methods are described (Ebinuma 2000a,b). Additional positive selection markers, which confer a growth advantage to a transformed plant in comparison with a non-transformed one, are described e.g., in EP-A 0 601 092. Growth stimulation selection markers may include (but shall not be limited to) β-Glucuronidase (in combination with e.g., a cytokinin glucuronide), mannose-6-phosphate isomerase (in combination with mannose), UDP-galactose-4-epimerase (in combination with e.g., galactose), wherein mannose-6-phosphate isomerase in combination with mannose is especially preferred.

iii) Counter-Selection Marker

Counter-selection markers are especially suitable to select organisms with defined deleted sequences comprising said marker (Koprek 1999). Examples for counter-selection marker comprise thymidin kinases (TK), cytosine deaminases (Gleave 1999; Perera 1993; Stougaard 1993), cytochrom P450 proteins (Koprek 1999), haloalkan dehalogenases (Naested 1999), iaaH gene products (Sundaresan 1995), cytosine deaminase codA (Schlaman & Hooykaas 1997), or tms2 gene products (Fedoroff & Smith 1993).

4. Regeneration

After the embryogenic callus induction and selection period (as described above) the resulting maturing embryogenic callus is transferred to a medium allowing conversion of transgenic plantlets. Preferably such medium does not comprise auxins such as 2,4-D in a concentration leading to dedifferentiation.

In an preferred embodiment such medium may comprise one or more compounds selected from the group consisting of:
i) cytokinins such as for example zeatin, preferably in a concentration from about 0.5 to about 10 mg/L, more preferably from about 1.5 to about 5 mg/L,
ii) an effective amount of at least one antibiotic that inhibits or suppresses the growth of the soil-borne bacteria (as defined above), and
iii) an effective amount of a selection agent allowing for selection of cells comprising the transgenic T-DNA.

The embryogenic callus is preferably incubated on this medium until shoots are formed and then transferred to a rooting medium. Such incubation may take from 1 to 5, preferably from 2 to 3 weeks.

Regenerated shoots or plantlets (i.e., shoots with roots) are transferred to Phytatray or Magenta boxes containing rooting medium (such as the medium described by recipe A-8) and incubate until rooted plantlets have developed (usually 1 to 4 weeks, preferably 2 weeks). The rooted seedlings are transferred to Metromix soil and grown to mature plants as described in the art (see examples).

In a preferred embodiment of the invention an improved procedure is employed and plantlets regenerated on plates are directly transplanted to MetroMix in the greenhouse, omitting the step in the rooting box, thereby saving time and labor.

If needed putative transgenic plants are sprayed with the appropriate selection agent (such as 70 to 100 g/ha Pursuit™), and grown in the greenhouse for another two weeks. Non-transgenic plants should develop herbicidal symptoms or die in this time. Survived plants are transplanted into pots with MetroMix soil.

The resulting plants can be bred and hybridized in the customary fashion. Two or more generations should be grown in order to ensure that the genomic integration is stable and hereditary. For example, at the flowering stage, the tassels of transgenic plants are bagged with brown paper bags to prevent pollen escape. Pollination is performed on the transgenic plants. It is best to do self-pollination on the transgenic plants. If silking and antithesis are not synchronized, a wild-type pollen donor or recipient plant with same genetic background as the transgenic $T_0$ plant should be available for performing cross-pollination. $T_1$ seeds are harvested, dried and stored properly with adequate label on the seed bag. After harvesting the transgenic $T_1$ seeds, $T_0$ plants including the soil and pot should be bagged in autoclave bags and autoclaved (double bagging).

Other important aspects of the invention include the progeny of the transgenic plants prepared by the disclosed methods, as well as the cells derived from such progeny, and the seeds obtained from such progeny.

5. Preferred Genetic Components and T-DNAs

Preferably, the genetic component (e.g., the T-DNA) inserted into the genome of the target plant comprises at least one expression cassette, which may—for example—facilitate expression of selection markers, trait genes, antisense RNA or double-stranded RNA. Preferably said expression cassettes comprise a promoter sequence functional in plant cells operatively linked to a nucleic acid sequence which— upon expression—confers an advantageous phenotype to the so transformed plant. The person skilled in the art is aware of numerous sequences which may be utilized in this context, e.g. to increase quality of food and feed, to produce chemicals, fine chemicals or pharmaceuticals (e.g., vitamins, oils, carbohydrates; Dunwell 2000), conferring resistance to herbicides, or conferring male sterility. Furthermore, growth, yield, and resistance against abiotic and biotic stress factors (like e.g., fungi, viruses or insects) may be enhanced. Advantageous properties may be conferred either by overexpressing proteins or by decreasing expression of endogenous proteins by e.g., expressing a corresponding antisense (Sheehy 1988; U.S. Pat. No. 4,801,340; Mol 1990) or double-stranded RNA (Matzke 2000; Fire 1998; Waterhouse 1998; WO 99/32619; WO 99/53050; WO 00/68374; WO 00/44914; WO 00/44895; WO 00/49035; WO 00/63364).

For expression in plants, plant-specific promoters are preferred. The term "plant-specific promoter" is understood as meaning, in principle, any promoter which is capable of governing the expression of genes, in particular foreign genes, in plants or plant parts, plant cells, plant tissues or plant cultures. In this context, expression can be, for example, constitutive, inducible or development-dependent. The following are preferred:

a) Constitutive Promoters

"Constitutive" promoters refers to those promoters which ensure expression in a large number of, preferably all, tissues over a substantial period of plant development, preferably at all times during plant development. A plant promoter or promoter originating from a plant virus is especially preferably used. The promoter of the CaMV (cauliflower mosaic virus) 35S transcript (Franck 1980; Odell 1985; Shewmaker 1985; Gardner 1986) or the 19S CaMV promoter (U.S. Pat. No. 5,352,605; WO 84/02913; Benfey 1989) are especially preferred. Another suitable constitutive promoter is the rice actin promoter (McElroy 1990), Rubisco small subunit (SSU) promoter (U.S. Pat. No. 4,962,028), the legumin B promoter (GenBank Acc. No. X03677), the promoter of the nopalin synthase from *Agrobacterium*, the TR dual promoter, the OCS (octopine synthase) promoter from *Agrobacterium*, the ubiquitin promoter (Holtorf 1995), the ubiquitin 1 promoter (Christensen 1989, 1992; Bruce 1989), the Smas promoter, the cinnamyl alcohol dehydrogenase promoter (U.S. Pat. No. 5,683,439), the promoters of the vacuolar ATPase subunits, the pEMU promoter (Last 1991); the MAS promoter (Velten 1984) and maize H3 histone promoter (Lepetit 1992; Atanassova 1992), the promoter of the *Arabidopsis thaliana* nitrilase-1 gene (GenBank Acc. No.: U38846, nucleotides 3862 to 5325 or else 5342) or the promoter of a proline-rich protein from wheat (WO 91/13991), and further promoters of genes whose constitutive expression in plants, especially in monocot or Gramineae plants is known to the skilled worker. The maize ubiquitin promoter is particularly preferred in wheat and barley.

b) Tissue-Specific or Tissue-preferred Promoters

Furthermore preferred are promoters with specificities for seeds, such as, for example, the phaseolin promoter (U.S. Pat. No. 5,504,200; Bustos 1989, Murai 1983; Sengupta-Gopalan 1985), the promoter of the 2S albumin gene (Joseffson 1987), the legumine promoter (Shirsat 1989), the USP (unknown seed protein) promoter (Bäumlein 1991a), the napin gene promoter (U.S. Pat. No. 5,608,152; Stalberg 1996), the promoter of the sucrose binding proteins (WO 00/26388) or the legumin B4 promoter (LeB4; Bäumlein 1991b, 1992), the *Arabidopsis* oleosin promoter (WO 98/45461), and the *Brassica* Bce4 promoter (WO 91/13980). Promoters which are furthermore preferred are those which permit a seed-specific expression in monocots such as maize, barley, wheat, rye, rice and the like. The promoter of the lpt2 or lpt1 gene (WO 95/15389, WO 95/23230) or the promoters described in WO 99/16890 (promoters of the hordein gene, the glutelin gene, the oryzin gene, the prolamin gene, the gliadin gene, the glutelin gene, the zein gene, the casirin gene or the secalin gene) can advantageously be employed. Further preferred are a leaf-specific and light-induced promoter such as that from cab or rubisco (Simpson 1985; Timko 1985); an another-specific promoter such as that from LAT52 (Twell 1989b); a pollen-specific promoter such as that from ZmI3 (Guerrero 1993); and a microspore-preferred promoter such as that from apg (Twell 1993).

c) Chemically Inducible Promoters

The expression cassettes may also contain a chemically inducible promoter (review article: Gatz 1997), by means of which the expression of the exogenous gene in the plant can be controlled at a particular point in time. Such promoters such as, for example, the PRP1 promoter (Ward 1993), a salicylic acid-inducible promoter (WO 95/19443), a benzenesulfonamide-inducible promoter (EP 0 388 186), a tetracyclin-inducible promoter (Gatz 1991, 1992), an abscisic acid-inducible promoter EP 0 335 528) or an ethanol-cyclohexanone-inducible promoter (WO 93/21334) can likewise be used. Also suitable is the promoter of the glutathione-S transferase isoform 11 gene (GST-II-27), which can be activated by exogenously applied safeners such as, for example, N,N-diallyl-2,2-dichloroacetamide (WO 93/01294) and which is operable in a large number of tissues of both monocots and dicots. Further exemplary inducible promoters that can be utilized in the instant invention include that from the ACE1 system which responds to copper (Mett 1993); or the In2 promoter from maize which responds to benzenesulfonamide herbicide safeners (Hershey 1991; Gatz 1994). A promoter that responds to an inducing agent to which plants do not normally respond can be utilized. An exemplary inducible promoter is the inducible promoter from a steroid hormone gene, the transcriptional activity of which is induced by a glucocorticosteroid hormone (Schena 1991).

Particularly preferred are constitutive promoters. Furthermore, further promoters may be linked operably to the nucleic acid sequence to be expressed, which promoters make possible the expression in further plant tissues or in other organisms, such as, for example, *E. coli* bacteria. Suitable plant promoters are, in principle, all of the above-described promoters.

The genetic component and/or the expression cassette may comprise further genetic control sequences in addition to a promoter. The term "genetic control sequences" is to be understood in the broad sense and refers to all those sequences which have an effect on the materialization or the function of the expression cassette according to the invention. For example, genetic control sequences modify the transcription and translation in prokaryotic or eukaryotic organisms. Preferably, the expression cassettes according to the invention encompass a promoter functional in plants 5'-upstream of the nucleic acid sequence in question to be expressed recombinantly, and 3'-downstream a terminator sequence as additional genetic control sequence and, if appropriate, further customary regulatory elements, in each case linked operably to the nucleic acid sequence to be expressed recombinantly.

Genetic control sequences furthermore also encompass the 5'-untranslated regions, introns or noncoding 3'-region of genes, such as, for example, the actin-1 intron, or the Adh1-S introns 1, 2 and 6 (general reference: The Maize Handbook, Chapter 116, Freeling and Walbot, Eds., Springer, N.Y. (1994)). It has been demonstrated that they may play a significant role in the regulation of gene expression. Thus, it has been demonstrated that 5'-untranslated sequences can enhance the transient expression of heterologous genes. Examples of translation enhancers which may be mentioned are the tobacco mosaic virus 5' leader sequence (Gallie 1987) and the like. Furthermore, they may promote tissue specificity (Rouster 1998).

The expression cassette may advantageously comprise one or more enhancer sequences, linked operably to the promoter, which make possible an increased recombinant expression of the nucleic acid sequence. Additional advantageous sequences, such as further regulatory elements or terminators, may also be inserted at the 3' end of the nucleic acid sequences to be expressed recombinantly. Polyadenylation signals which are suitable as control sequences are plant polyadenylation signals, preferably those which essentially correspond to T-DNA polyadenylation signals from *Agrobacterium tumefaciens*, in particular the OCS (octopin synthase) terminator and the NOS (nopalin synthase) terminator.

Control sequences are furthermore to be understood as those permitting removal of the inserted sequences from the genome. Methods based on the cre/lox (Sauer 1998; Odell 1990; Dale 1991), FLP/FRT (Lysnik 1993), or Ac/Ds system (Wader 1987; U.S. Pat. No. 5,225,341; Baker 1987; Lawson 1994) permit a—if appropriate tissue-specific and/or inducible—removal of a specific DNA sequence from the genome of the host organism. Control sequences may in this context mean the specific flanking sequences (e.g., lox sequences), which later allow removal (e.g., by means of cre recombinase).

The genetic component and/or expression cassette of the invention may comprise further functional elements. The term functional element is to be understood in the broad sense and refers to all those elements which have an effect on the generation, amplification or function of the genetic component, expression cassettes or recombinant organisms according to the invention. Functional elements may include for example (but shall not be limited to):

1) Selection markers as described above.
2) Reporter genes

Reporter genes encode readily quantifiable proteins and, via their color or enzyme activity, make possible an assessment of the transformation efficacy, the site of expression or the time of expression. Very especially preferred in this context are genes encoding reporter proteins (Schenborn 1999) such as the green fluorescent protein (GFP) (Sheen 1995; Haseloff 1997; Reichel 1996; Tian 1997; WO 97/41228; Chui 1996; Leffel 1997), chloramphenicol transferase, a luciferase (Ow 1986; Millar 1992), the aequorin gene (Prasher 1985), β-galactosidase, R locus gene (encoding a protein which regulates the production of anthocyanin pigments (red coloring) in plant tissue and thus makes possible the direct analysis of the promoter activity without addition of further auxiliary substances or chromogenic substrates (Dellaporta 1988; Ludwig 1990), with β-glucuronidase (GUS) being very especially preferred (Jefferson 1987a,b). β-glucuronidase (GUS) expression is detected by a blue color on incubation of the tissue with 5-bromo-4-chloro-3-indolyl-β-D-glucuronic acid, bacterial luciferase (LUX) expression is detected by light emission; firefly luciferase (LUC) expression is detected by light emission after incubation with luciferin; and galactosidase expression is detected by a bright blue color after the tissue is stained with 5-bromo-4-chloro-3-indolyl-β-D-galactopyranoside. Reporter genes may also be used as scorable markers as alternatives to antibiotic resistance markers. Such markers are used to detect the presence or to measure the level of expression of the transferred gene. The use of scorable markers in plants to identify or tag genetically modified cells works well only when efficiency of modification of the cell is high.

3) Origins of replication, which ensure amplification of the expression cassettes or vectors according to the invention in, for example, *E. coli*. Examples which may be mentioned are ORI (origin of DNA replication), the pBR322 ori or the P15A ori (Maniatis 1989).

4) Elements which are necessary for *Agrobacterium*-mediated plant transformation, such as, for example, the right or left border of the T-DNA or the vir region.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All publications, patents, and patent applications cited herein are hereby incorporated by reference for all purposes.

Sequences

1. SEQ ID NO: 1 Binary vector pPBS_MM232
2. SEQ ID NO: 2 Nucleic acid sequence coding for XA17 mutant of ahas selection marker.
3. SEQ ID NO: 3 Amino acid sequence coding for XA17 mutant of ahas selection marker.

Deposit Under the Budapest Treaty

A deposit was made under the Budapest Treaty for the following material:

1. Seed of *Zea mays* line BPS553; Patent Deposit Designation PTA-6170.
2. Seed of *Zea mays* line BPS631; Patent Deposit Designation PTA-6171.

The deposit was made with the American Type Culture Collection (ATCC), Manassas, Va. 20110-2209 USA on Aug. 26, 2004.

EXAMPLES

General Methods:

Unless indicated otherwise, chemicals and reagents in the Examples were obtained from Sigma Chemical Company (St. Louis, Mo.). Materials for cell culture media were obtained from Gibco/BRL (Gaithersburg, Md.) or DIFCO (Detroit, Mich.). The cloning steps carried out for the purposes of the present invention, such as, for example, transformation of *E. coli* cells, growing bacteria, multiplying phages and sequence analysis of recombinant DNA, are carried out as described by Sambrook (1989). The following examples are offered by way of illustration and not by way of limitation.

Media Recipes

Imazethapyr (Pursuit) stock solution (1 mM) is prepared by dissolving 28.9 mg of Pursuit into 100 ml of DMSO (Sigma), and stored at 4° C. in the dark. Acetosyringone stock is prepared as 200 mM solution in DMSO and stored at −20° C.

A-1. Maize YP Media (for Growing *Agrobacterium*)

| Media Components | Final Concentration |
|---|---|
| Yeast extract | 5 g/L |
| Peptone (from meat) | 10 g/L |
| NaCl | 5 g/L |

Adjust pH to 6.8 with 1 M NaOH. For solid medium add 3 g agar (EM Science) per 250 mL bottle. Aliquot 100 mL media to each 250 mL bottle, autoclave, let cool and solidify in bottles. For plate preparation, medium in bottle is melted in microwave oven, and the bottle is placed in water bath and cool to 55° C. When cooled, add spectinomycin (Sigma S-4014) to a final concentration of 50 mg/l mix well and pour the plates.

A-2. Maize LS-Inf Medium

| Media Components | Final Concentration |
|---|---|
| MS (Murashige and Skoog basal media) M-5524 | 4.3 g/L |
| Vitamin assay casamino acids (Difco) | 1.0 g/L |
| Glucose | 36 g/L |
| Sucrose | 68.5 g/L |
| 2,4-D (stock at 0.5 mg/mL) | 1.5 mg/L |
| Nicotinic acid (stock 0.5 mg/mL) sterile | 0.5 mg/L |
| Pyridoxine HCl (0.5 mg/mL) sterile | 0.5 mg/L |
| Thiamine HCl (1.0 mg/mL) sterile | 1.0 mg/L |
| Myo-inositol (100 mg/mL) sterile | 100 mg/L |

Adjust pH to 5.2 with 1 M HCl, filter sterilize, dispense in 100 mL aliquots, add acetosyringone (100 μM) to the medium right before used for *Agrobacterium* infection (50 μL to 100 mL media-200 mM stock).

A-3. Maize 1.5LSAs Medium (for Co-cultivation)

| Media Components | Final Conc. |
|---|---|
| MS (Murashige and Skoog basal media) M-5524 | 4.3 g/L |
| Glucose | 10 g/L |
| Sucrose | 20 g/L |
| 2,4-D (stock at 0.5 mg/mL) | 1.5 mg/L |
| Nicotinic acid (stock 0.5 mg/mL) sterile | 0.5 mg/L |
| Pyridoxine HCl (0.5 mg/mL) sterile | 0.5 mg/L |
| Thiamine HCl (1.0 mg/mL) sterile | 1.0 mg/L |
| Myo-inositol (100 mg/mL) sterile | 100 mg/L |
| L-proline (stock 350 mg/mL) | 700 mg/L |
| MES (stock 250 mg/mL) | 500 mg/L |

Adjust pH media to 5.8 with 1 M NaOH. Weigh 4 g Sigma Purified Agar per bottle (8 g/L) and dispense 500 mL media per bottle, autoclave. When cooled add AgNO3 (stock at 15 mM) to a final concentration of 15 μM and L-cysteine (stock at 150 mg/ml) to a final concentration 300 mg/l. Pour into 100×20 mm Petri plates. Medium containing acetosyringone should be used freshly without long term storage.

A4. Maize Recovery Medium-1: IM medium

| Media Components | Final Conc. |
|---|---|
| MS (Murashige and Skoog basal media) M-5524 | 4.3 g/l |
| Sucrose | 30 g/l |
| 2,4D (stock 0.5 mg · ml) | 1.5 mg/ml |
| Casein hydrolysate | 100 mg/l |
| Proline | 2.9 g/l |

Measure ~¾ of the total volume ddH$_2$O desired, add sucrose and salts, and dissolve under stirring. After all ingredients are dissolved, adjust to final volume with ddH$_2$O and to pH 5.8 using 1M KOH. Aliquot 500 mls into 1 L bottle, add 0.9 g gelrite to each bottle of liquid, autoclave for 20 minutes (liquid cycle). After autoclaving place bottles into a water-bath to cool to 55° C. and add MS Vitamins (to final concentration of 1.0 mg/ml), silver nitrate (to final concentration of 15 μM) and Timentin (to final concentration of 150 mg/l). Pour media into 100×20 mm petri plates and allow media to remain in the laminar hood overnight to prevent excess condensation.

A-5. Maize Recovery Medium-2: MS Medium

| Media Components | Final Concentration |
|---|---|
| MS (Murashige and Skoog basal media) M-5524 | 4.3 g/L |
| Sucrose | 20 g/L |
| 2,4-D (stock at 2.0 mg/mL) | 1.5 mg/L |
| Nicotinic acid (stock 0.5 mg/mL) sterile | 0.5 mg/L |
| Pyridoxine HCl (0.5 mg/mL) sterile | 0.5 mg/L |
| Thiamine HCl (1.0 mg/mL) sterile | 1.0 mg/L |
| Myo-inositol (100 mg/mL) sterile | 100 mg/L |
| L-proline (stock 350 mg/mL) | 700 mg/L |
| MES (stock 250 mg/mL) | 500 mg/L |

Adjust pH of media to pH 5.8 with 1 M NaOH. Add Sigma Purified Agar per bottle (8 g/L). Dispense 500 mL media per bottle, autoclave. When cooled add silver nitrate (to final concentration of 15 μM) and Timentin (to final concentration of 150 mg/l). This recovery medium is especially suitable for BPS553×(HiIIA×A188) or BPS631×(HiIIA×A188) genotypes.

A-6. Selection Media

| Media Components | Final Concentration |
|---|---|
| MS (Murashige and Skoog basal media) M-5524 | 4.3 g/L |
| Sucrose | 20 g/L |
| 2,4-D (stock at 2.0 mg/mL) | 0.5 mg/L |
| Nicotinic acid (stock 0.5 mg/mL) sterile | 0.5 mg/L |
| Pyridoxine HCl (0.5 mg/mL) sterile | 0.5 mg/L |
| Thiamine HCl (1.0 mg/mL) sterile | 1.0 mg/L |
| Myo-inositol (100 mg/mL) sterile | 100 mg/L |
| L-proline (stock 350 mg/mL) | 700 mg/L |
| MES (stock 250 mg/mL) | 500 mg/L |

Adjust pH of media to pH 5.8 with 1 M NaOH. Add Sigma Purified Agar (8 g/L), dispense 500 mL media per 1 L bottle, autoclave, when cooled add:

| Medium type | Post autoclaving components | Final Concentration |
|---|---|---|
| 1$^{st}$ selection | Timentin (stock at 200 mg/ml) | 150 mg/l |
| | Pursuit (stock at 1 mM) | 500 nM |
| | Picloram (2 mg/ml) | 2 mg/l |

| Medium type | Post autoclaving components | Final Concentration |
|---|---|---|
| 2nd selection | Timentin (stock at 200 mg/ml) | 150 mg/l |
| | Pursuit (stock at 1 mM) | 750 nM |
| | Picloram (2 mg/ml) | 2 mg/l |

A-7. Maize Regeneration Media

| Media Components | Final Concentration |
|---|---|
| MS (Murashige and Skoog basal media) M-5524 | 4.3 g/L |
| Sucrose | 20 g/L |
| Nicotinic acid (stock 0.5 mg/mL) sterile | 0.5 mg/L |
| Pyridoxine HCl (0.5 mg/mL) sterile | 0.5 mg/L |
| Thiamine HCl (1.0 mg/mL) sterile | 1.0 mg/L |
| Myo-inositol (100 mg/mL) sterile | 100 mg/L |
| L-proline (stock 350 mg/mL) | 700 mg/L |
| MES (stock 250 mg/mL) | 500 mg/L |

Adjust pH media to 5.8 with 1 M NaOH. Weigh 4 g Sigma Purified Agar per bottle (8 g/L). Dispense 500 mL media per bottle, autoclave and let solidify in bottles. For use, microwave to melt media, when cooled, add

| Post autoclaving components | Final Concentration |
|---|---|
| Timentin (200 mg/ml) | 150 mg/l |
| Pursuit (stock at 1 mM) | 500 nM |
| Zeatin (stock at 5 mg/mL) | 2.5 mg/l |

Pour into 100×20 mm Petri plates

A-8. Maize Rooting Media (Rooting)

| Media Components | Final Concentration |
|---|---|
| ½ MS (Murashige and Skoog basal media) M-5524 | 2.15 g/L |
| Sucrose | 20 g/L |
| Nicotinic acid (stock 0.5 mg/mL) sterile | 0.5 mg/L |
| Pyridoxine HCl (0.5 mg/mL) sterile | 0.5 mg/L |
| Thiamine HCl (1.0 mg/mL) sterile | 1.0 mg/L |
| Myo-inositol (100 mg/mL) sterile | 100 mg/L |
| L-proline (stock 350 mg/mL) | 700 mg/L |
| MES (stock 250 mg/mL) | 500 mg/L |

Adjust pH of media to pH 5.8 with 1 M NaOH, add 1 g Gelrite per bottle (2 g/L), dispense 500 mL media per bottle, autoclave, pour into disposable Phyatrays.

| M-LS-301 | | |
|---|---|---|
| Ingredients (stock conc.) | Cat. #/ Supplier | Final conc. Amt Units |
| MS salts | Sigma M5524 | 4.3 g/L |
| Sucrose | Sigma S5391 | 20 g/L |
| 2,4-D (stk 0.5 mg/ml) | Sigma D7299 | 1.5 mg/L |
| Nicotinic acid (stk 0.5 mg/ml) | Sigma N4126 | 0.5 mg/L |
| Pyridoxine HCl (stk 0.5 mg/mL) | Sigma P8666 | 0.5 mg/L |
| Thiamine HCl (stk 1.0 mg/mL) | Sigma T4625 | 1 mg/L |
| Myo-inositol (stk 100 mg/mL) | Sigma I5125 | 100 mg/L |
| L-proline (stk 350 mg/mL) | Sigma P5607 | 700 mg/L |
| MES | Sigma M3671 | 500 mg/L |
| Purified Agar** | Sigma A7921 | 8 g/l |
| pH 5.8, autoclave | | |
| After autoclave add the ff: | | |
| Timentin (stk 200 mg/ml) | Bellamy DS | 150 mg |
| for 0.5 P, PURSUIT (stk 1 mM) | AC263, 499 | 0.5 uM |

| M-LS-401 | | |
|---|---|---|
| Ingredients (stock conc.) | Cat. #/ Supplier | Final conc. Amt Units |
| MS salts | Sigma M5524 | 4.3 g/L |
| Sucrose | Sigma S5391 | 20 g/L |
| 2,4-D (stk 0.5 mg/ml) | Sigma D7299 | 1.5 mg/L |
| Nicotinic acid (stk 0.5 mg/ml) | Sigma N4126 | 0.5 mg/L |
| Pyridoxine HCl (stk 0.5 mg/mL) | Sigma P8666 | 0.5 mg/L |
| Thiamine HCl (stk 1.0 mg/mL) | Sigma T4625 | 1 mg/L |
| Myo-inositol (stk 100 mg/mL) | Sigma I5125 | 100 mg/L |
| L-proline (stk 350 mg/mL) | Sigma P5607 | 700 mg/L |
| MES | Sigma M3671 | 500 mg/L |
| Purified Agar** | Sigma A7921 | 8 g/l |
| pH 5.8, autoclave | | |
| After autoclave add the ff: | | |
| Timentin (stk 200 mg/ml) | Bellamy DS | 150 mg |
| for 0.75 P, PURSUIT (stk 1 mM) | AC263, 499 | 0.75 uM |

| M-LS-503 | | |
|---|---|---|
| Ingredients (stock conc.) | Cat. #/ Supplier | Final conc. Amt Units |
| MS salts | Sigma M5524 | 4.3 g/L |
| Sucrose | Sigma S5391 | 20 g/L |
| Nicotinic acid (stk 0.5 mg/ml) | Sigma N4126 | 0.5 mg/L |
| Pyridoxine HCl (stk 0.5 mg/mL) | Sigma P8666 | 0.5 mg/L |
| Thiamine HCl (stk 1.0 mg/mL) | Sigma T4625 | 1 mg/L |
| Myo-inositol (stk 100 mg/mL) | Sigma I5125 | 100 mg/L |
| Zeatin (stk 5 mg/ml) | Sigma Z0876 | 5 mg/L |
| L-proline (stk 350 mg/mL) | Sigma P5607 | 700 mg/L |
| MES | Sigma M3671 | 500 mg/L |
| Purified Agar** | Sigma A7921 | 8 g/l |
| pH 5.8, autoclave | | |
| After autoclave add the ff: | | |
| PURSUIT (stk 1 mM) | AC263, 499 | 0.75 uM |

| M-LS-504 | | |
|---|---|---|
| Ingredients (stock conc.) | Cat. #/ Supplier | Final conc. Amt Units |
| MS salts | Sigma M5524 | 4.3 g/L |
| Sucrose | Sigma S5391 | 30 g/L |
| Nicotinic acid (stk 0.5 mg/ml) | Sigma N4126 | 0.5 mg/L |
| Pyridoxine HCl (stk 0.5 mg/mL) | Sigma P8666 | 0.5 mg/L |
| Thiamine HCl (stk 1.0 mg/mL) | Sigma T4625 | 1 mg/L |
| Myo-inositol (stk 100 mg/mL) | Sigma I5125 | 100 mg/L |
| L-proline (stk 350 mg/mL) | Sigma P5607 | 700 mg/L |

-continued

| M-LS-504 | | |
|---|---|---|
| Ingredients (stock conc.) | Cat. #/ Supplier | Final conc. Amt Units |
| MES | Sigma M3671 | 500 mg/L |
| Purified Agar** | Sigma A7921 | 8 g/l |
| pH 5.8, autoclave | | |
| After autoclave add the ff: | | |
| PURSUIT (stk 1 mM) | AC263, 499 | 0.75 uM |
| Kinetin (stk 1 mg/mL) | Sigma K-3253 | 0.5 mg/L |
| Timentin (stk 200 mg/ml) | Bellamy DS | 150 mg/L |

Summary of Basic Protocol

This protocol works for all *Zea mays* lines (incl. both hybrid lines and inbred lines).

| Transformation phase | Methods | Media used | Conditions |
|---|---|---|---|
| *Agrobacterium* inoculation | 1.1 Modified "Tube" | LS-Inf liquid with 100-200 nM Acetosyringone | Dissect immature embryos directly into *Agrobacterium* suspension |
| | 1.2 The "Drop" method | LS-Inf + 100-200 nM Acetosyringone for preparing *Agrobacterium* cell suspension | Dissect immature embryos directly onto agar co-cultivation medium, and apply a drop (ca. 5 ul) of *Agrobacterium* cell suspension (OD600 = 0.5-2.0). |
| Co-cultivation | | 1.5LSAs Medium with 15 mM AgNO3, and 150-300 mg/l L-cysteine | Incubate culture at 22 C. in the dark for 1-3 days, typically 2-3 days. |
| Recovery | 3.1 | MS medium with 150 mg/l timentin, and 15 uM AgNO3 | Incubate cultures at 25-27 C. in the dark for 5-7 days |
| | 3.2 | IM medium (MS medium with 15 uM AgNO3, 2.7 g proline, 150 mg/l Timentin | Incubate cultures at 25-27 C. in dark for 5-7 days |
| Selection | 1st selection | MS medium with 500-750 nM Pursuit, 150 mg/l Timentin, 0.5 mg/l 2,4-D and 2 mg/l Picloram | Incubate cultures at 25-27 C. in dark for 14 days |
| | 2nd selection | MS medium with 750-1000 nM Pursuit, 150 mg/l Timentin, 0.5 mg/l 2,4-D and 2 mg/l Picloram | Incubate cultures at 25-27 C. in dark for 14 days |
| Regeneration | | MS medium with 500-750 nM Pursuit, 2.5 mg/l Zeatin and 150 mg/l Timentin | Incubate cultures at 25-27 C. in light for 14 days |
| Rooting | | ½ MS medium with 150 mg Timentin and 500 nM Pursuit | Incubate cultures at 25-27 C. in light for 14 days |

Example 1

Preparation of Hybrid Donor Plants

The following *Zea mays* inbred lines are employed for the following steps:

1. HiIIA: HiII parent A; deposit No.:T0940A, Maize Genetics and Genomics Database), available from Maize Genetics Cooperation—Stock Center USDA/ARS & Crop Sci/UIUC, S-123 Turner Hall, 1102 S. Goodwin Avenue, Urbana Ill. USA 61801-4798; maizegdb.org/stock.php.
2. A188: Agronomy & Plant Genetics, 411 Borlaug Hall, Univ of Minnesota, Saint Paul Minn. 55108.
3. BPS553 (ATCC Patent Deposit Designation PTA-6170)
4. BPS631 (ATCC Patent Deposit Designation PTA-6171)

F1 seeds of corn genotype HiIIA×A188 are produced by crossing HiIIA (female parent) with inbred line A188 (male), and planted in the greenhouse as pollen donor. F2 seeds of (HiIIA×A188) are produced by self-pollination of F1 (HiIIA×A188) plants either in the greenhouse or in the field, and planted in the greenhouse as the pollen donor. Hybrid immature embryos of BPS553×(HiIIA×A188) or BPS631×(HiIIA×A188) are produced using inbred line BPS553 (ATCC Patent Deposit Designation PTA-6170) or BPS631 (ATCC Patent Deposit Designation PTA-6171) as the female parents, and either F1 or F2 (HiIIA×A188) plants as the male parent in the greenhouse.

Seeds are sowed in pots containing Metromix. Once the seeds become germinated and rooted, one seedling/pot is maintained for immature embryo production, and the second seedling is discarded; Alternatively seeds are started in a 4×4 inch pots, and seedlings are transplanted to 10-inch pots two weeks after sowing the seeds. Approximately one tablespoon of Osmocote 14-14-14 (a type of slow releasing fertilizer) is added to the surface of each pot. The temperature in the greenhouse is maintained at 24° C. night and 28° C. day. Watering is done automatically, but is supplemented daily manually as needed. Twice a week, the plants are watered with a 1:15 dilution of Peters 20-20-20 fertilizer.

1.1 Preparation of Inbred Donor Plants

Seeds of inbred lines BPS553 or BPS631 are sown either directly in 4-inch pots, and the seedlings are transplanted to 10-inch pots two weeks after sowing the seeds. Alternatively, seeds are directly sown into 10-inch pots. Self- or sib-pollination is performed. The growing conditions are same as above for the hybrid line.

1.2 Hand-Pollination

Every corn plant is monitored for ear shoots, and when appeared, they are covered with a small white ear shoot bag (Lawson). Once the ear shoots have started to pro-duce silks, the silks are cut and covered again with the ear shoot bag. The tassel of the same plant is bagged with a brown paper bag (providing that the tassel has entered antithesis). The next morning, the tassel is shaken to remove pollen and anthers into the bag. The bag is then removed and pollen is shaken over the silks of the ear shoot. Pollinating is done between 8 and 10 a.m. in the morning. Secure the brown paper bag over the ear shoot and around the corn stalk. After pollination, the tassel is removed from the plant to reduce pollen (allergens to many people) in the greenhouse.

To ensure synchronized pollinations for the same genotypes, and hence to avoid weekend harvesting/transformation, ear shoots of those early flowering plants are cut back again. A group of plants, e.g. >5 to 10 plants are then pollinated on the same day. However, this practice is dependent on the quality/quantity of pollens on a plant. Sib-pollination is needed for the inbred lines. For instance either BPS553 or BPS631 can be either selfed or sib-pollinated between the same genotype).

1.3 Harvest and Pre-treat Ears

Ears from corn plants (the first ear that comes out is the best) are harvested 8 to 14 (average 10) days after pollination (DAP). Timing of harvest varies depending on growth conditions and maize variety. The size of immature embryos is a good indication of their stage of development. The optimal length of immature embryos for transformation is about 1 to 1.5 mm, including the length of the scutellum. The embryo should be translucent, not opaque. If the ear is ready, but can not be used for transformation that day, the ear can be harvested, put in the pollination bag, and stored in a plastic bag in 4° C. fridge for 1 to 3 days.)

2. Preparation of *Agrobacterium*

*Agrobacterium* glycerol stock is stored at −80° C. Inoculums of *Agrobacterium* are streaked from glycerol stocks onto YP agar medium (A-1) containing appropriate antibiotics (e.g. 50 mg/l spectinomycin and/or 10 mg/l tetracycline). The bacterial cultures are incubated in the dark at 28° C. for 1 to 3 days, or until single colonies are visible. The obtained plate can be stored at 4° C. for 1 month and used as a master plate to streak out fresh cells. Fresh cells should be streaked onto YP agar with the appropriate antibiotic from a single colony on the master plate, at least 2 days in advance of transformation. These bacterial cultures can be incubated in the dark at 28° C. for 1 to 3 days.

Alternatively frozen *Agrobacterium* stock can be prepared: Streak *Agrobacterium* cells from frozen stock to a plate B-YP-002 (YP+50 mg/l spectinomycin+10 mg/l tetracycline). Grow at 28° C. for 2 to 3 days. Save it as master plate and store at 4 C. for up to a month. From the master plate, streak a loop of agro cells to a flask containing 25 ml liquid B-YP-000 medium supplemented with 50 mg/l Spectinomycin+10 mg/l tetracycline. Grow on a shaker set at 300 rpm and 28° C. 2 to 3 days. Prepare frozen agro stock by mixing 1 part of the above agro culture with 1 part of sterile 30% glycerol. Vortex to mix well and dispense 10 µl the *Agrobacterium*/glycerol mixture to a 50 µl Eppendorf tube. Store at −80° C.

One to two loops full (2 mm in diameter) of bacterial culture is suspended in 1.0 to 1.8 ml LS-inf medium supplemented with 100 µM acetosyringone. This yields a bacterial suspension with approximate optical density ($OD_{600}$) between 0.5 to 2.0. Vortex for 0.5 to 3 hours. Vortexing is performed by fixing (e.g. with tape) the microfuge tube horizon-tally (instead of vertically) on the platform of a vortexer to ensure better disperse *Agrobacterium* cells into the solution. Mix 100 µl of *Agrobacterium* cell suspension with 900 ul of LS-inf solution in a curvet, and measure $OD_{600}$. Adjust OD of original *Agrobacterium* solution to 0.6 to 2.0 with LS-Inf (with 100 µM acetosyringone) solution. The *Agrobacterium* suspension is preferably vortexed in the LS-inf+acetosyringone media for at least 0.5 to 3 hours prior to infection. Prepare this suspension before starting harvesting embryos.

Alternatively *Agrobacterium* suspensions for corn transformation can be prepared as follows: Two days before transformation, from −80° C. stock, streak *Agrobacteria* from one tube to a plate containing B-YP-002 (solidified YP+50 mg/l spectinomycin+10 mg/l tetracycline) and grow at 28° C. in the dark for two days. About 1 to 4 hrs before transformation, place one scoop of bacterial cells to 1.5 ml M-LS-002 medium (LSinf+200 µM acetosyrigone) in a 2 ml Eppendorf tube. Vortex the tube to dispense the bacterial cells to solution and shake the tube at 1000 rpm for 1 to 4 hrs. The $OD_{600}$ should be in the range of 0.6 to 1.0 or about $10^8$ cfu/mL.

For the purpose of the following examples *Agrobacterium tumefaciens* strain LBA4404 or disarmed *Agrobacterium* strain K599 (NCPPB 2659)) transformed with binary vector plasmid pBPSMM232 were employed. pBPS_MM232 contains the ahas gene (as selection marker) and the gus reporter gene.

Example 3

Isolation of Immature Embryos 3.1 Surface Sterilization

The ears are harvested from the greenhouse 8 to 12 days after pollination. All husk and silks are removed and ears are transported in the brown pollination bag back to the tissue culture lab. The cob is moved into the sterile hood. A large pair of forceps is inserted into the basal end of the ear and the forceps are used as a handle for handling the cob. Optionally, when insects/fungus are present on the ear, the ear should be first sterilized with 20% commercial bleach for 10 min (alternatively 30% Clorox solution for 15 min), and then rinsed with sterilized water three times. While holding the cob by the forceps, the ear is completely sprayed with 70% ethanol and then rinsed with sterile dd$H_2O$.

3.2. Preparation and *Agrobacterium* Inoculation of Immature Embryos 3.2.1 Method-1: The Modified "Tube" Method The cob with the forceps handle is placed in a large Petri plate. A dissecting scope may be used. The top portion (⅔'s) of kernels are cut off and removed with a #10 scalpel (for safety consideration, the cut on the kernels is made by cutting away from your hand that holds the handle of the forceps). The immature embryos are then excised from the kernels on the cob with a scalpel (#11 scalpel): the scalpel blade is inserted on an angle into one end of the kernel. The endosperm is lifted upwards; the embryo is lying underneath the endosperm. The excised embryos are collected in a microfuge tube (or a small Petri plate) containing roughly 1.5 to 1.8 ml of *Agrobacterium* suspension in LS-inf liquid medium containing acetosyrigone (see above; medium A-2). Each tube can contain up to 100 embryos. The tube containing embryos is hand-mixed several times, and let the tube/plate stand at room temperature (20 to 25° C.) for 30 min. Remove excess bacterial suspension from the tube/plate with a pipette. Transfer the immature embryos and bacteria in the residue LS-inf medium to a Petri plate containing co-cultivation agar medium. Transfer any immature embryos that remain in the microfuge tube by a sterile loop. Remove excess bacterial suspension with a pipette. A small amount of liquid is preferably be left in the plate to avoid drying out the embryos while plating. Place the immature embryos on the co-cultivation medium with the flat side down (scutellum upward). Do not embed the embryos into medium. Leave the plate cover open in the sterile hood for about 15 min for evaporating excess moisture covering immature embryos. Seal the Petri dishes with 3M micropore tape. About 100 embryos can be placed on a Petri plate for co-cultivation. Seal the plate and wrap with a sheet of aluminum foil. Incubate the plates in the dark at 22° C. for 2 to 3 days. Take 3 to 5 immature embryos for GUS staining if a GUS construct is used to assess transient GUS expression.

3.2.2 Method-2: The "Drop" Method

Excised immature embryos are directly put on the co-cultivation medium (medium A-3) with the flat side down (scutellum upward). Each plate (20×100 mm plate) can hold up to 100 immature embryos. Put 5 μl of diluted *Agrobacterium* cell suspension to each immature embryo with a repeat pipettor. Remove excess moisture covering immature embryos by leaving the plate cover open in the hood for about 15 min. Seal the plate with 3M micropore tape and wrap with aluminum foil. Incubate the plate in the dark at 22° C. for 2 to 3 days. Take 3-5 immature embryos for GUS staining if a GUS construct is used to assess transient GUS expression.

TABLE 1

Comparison of two inoculation methods: "Drop" and modified "Tube" methods in two maize genotypes.

| Genotypes | Inoculation method | # Immature embryos | # Events | % Transformation efficiency |
|---|---|---|---|---|
| (HillAxA188) selfed | Modified Tube | 295 | 30 | 10 |
| | Drop | 293 | 30 | 10 |
| BPS553x (HillAxA188) | Modified Tube | 72 | 14 | 19.4 |
| | Drop | 84 | 19 | 22.6 |

It has been demonstrated (see results in table 2 below) that presence of a thiol compound such as L-cysteine in the co-cultivation medium significantly increasing transformation efficiency.

TABLE 2

Effect of L-cysteine on transformation efficiencies in the inbred BPS553 and the hybrid BPS553x(HillAxA188) lines. Transformation experiments were performed with split-cob (dividing a corn cob into two treatments: with or without adding L-cysteine) experimental design, and using the "drop" inoculation method described herein. Each experiments comprised of an average of 50-100 immature embryos.

| Genotype | L-Cysteine | # Experiments | Average TE (%) |
|---|---|---|---|
| BPS553x(HillAxA188) | + | 20 | 32.2* |
| | − | 20 | 12.6 |
| BPS553 | + | 27 | 9.6* |
| | − | 27 | 3.5 |

TE = transformation efficiency;
*Statistically significant at 95% confident level from the treatment without adding L-cysteine in the co-cultivation medium.

3.2.3 Application of Filter Paper During Co-cultivation

The immature embryos are excised from the kernels on the cob with a scalpel (#11 scalpel) as described above, and collected in a microfuge tube (or a small Petri plate) containing roughly 1.5 to 1.8 ml of *Agrobacterium* suspension in LS-inf liquid medium containing acetosyrigone (see above; medium A-2). Each tube can contain up to 100 embryos. The tube containing embryos is hand-mixed several times, and let the tube/plate stand at room temperature (20 to 25° C.) for 30 min. The excess bacterial suspension is removed from the tube/plate with a pipette, and the immature embryos in the residue LS-inf medium are transferred to the surface of a layer of filter paper that is placed on the agar co-cultivation medium. The immature embryos that remain in the microfuge tube are transferred to the filter paper on the co-cultivation medium by a sterile loop. The excess bacterial suspension in the co-cultivation plate was removed with a pipette. A small amount of liquid is preferably left in the plate to avoid drying out the embryos while plating. Place the immature embryos on the co-cultivation medium with the flat side down (scutellum upward). Leave the plate cover open in the sterile hood for about 15 min for evaporating excess moisture covering immature embryos. Seal the Petri dishes with 3M micropore tape. About 100 embryos can be placed on a Petri plate for co-cultivation. Seal the plate and wrap with a sheet of aluminum foil. Incubate the plates in the dark at 22° C. for 2 to 3 days. Take 3 to 5 immature embryos for GUS staining if a GUS construct is used to assess transient GUS expression.

TABLE 3

Effect of application of filter paper (FP) on the transformation in the BPS553 inbred line. One layer of filter paper was put on the surface of the co-cultivation agar medium containing 150 mg/l L-cysteine and 15 μM AgNO3 for the filter paper treatment. The control non-filter paper treatment was conducted exactly the same as the filter paper treatment except the filter paper was omitted. After the inoculation with the modified "Tube" inoculation method, the immature embryos (IEs) were placed on the filter paper.

| Treatment | # IEs infected | # Expts | Avg TE (%) | StdEv | p Value |
|---|---|---|---|---|---|
| +FP | 2004 | 24 | 9.5 | 9.3 | 0.0005 |
| −FP | 2126 | 24 | 2.8 | 3.8 | |

The co-cultivation condition was further tested under the agar-free medium condition by adding co-cultivation liquid medium solution to the multiple layers of filter paper in a plate. The advantages of using agar-free, filter paper only support include, but do not limit to (1) the reduced medium preparation time, and (2) the increased flexibility of altering the co-cultivation medium components.

Example 4

Recovery

After co-cultivation, transfer the embryos to recovery media (A-4 or A-5) and incubate the plates in dark at 27° C. for about 5 to 7 days. Keep scutellum side up and do not embed into the media.

TABLE 3

Effect of length of recovery (without adding selection agent in the medium) after co-cultivation on transformation efficiency in the genotype of BPS553x(HillAxA188). The average number of immature embryos for each treatment in a replicate was about 70.

| Days on Recovery medium | | % Transformation efficiency | | | | |
|---|---|---|---|---|---|---|
| without selection | with 750 nM Pursuit | Rep-1 | Rep-2 | Rep-3 | Rep-4 | Average % TE |
| 0 | 5 | 0 | 0 | 0 | 1 | 1 |
| 2 | 3 | 4 | 3 | 0 | 29 | 9 |
| 5 | 0 | 17 | 17 | 19 | 36 | 22.3 |
| 8 | 0 | 17 | 6 | 15 | 20 | 14.5 |

Example 5

Selection 5.1 Basic Selection Protocol Transfer immature embryos to $1^{st}$ selection media (A-6). Roughly 25 to 50 immature embryos can be placed on each plate. Be careful to maintain the same orientation of the embryos (scutellum up). Do not embed the embryos in the media. Seal the Petri plates with white tape. Incubate in the dark at 27° C. for 10 to 14 days (First selection). Subculture all immature embryos that produce variable calli to 2nd selection media (A-6). Try to avoid transferring slimy or soft calli. At this stage, use scissors to remove any shoots that have formed (try to remove the entire embryo from the scutellum if possible and discard it). Firmly place the callus on the media—do not embed into the media. Wrap the plates in 3M Micropore tape and put in the dark at 27° C. Incubate for 2 weeks under the same conditions for the first selection (Second selection). Using 2 pairs of fine forceps, excise the regenerable calli from the scutellum under a stereoscopic microscope. The regenerable calli is whitish/yellowish in color, compact, not slimy and may have some embryo-like structures. Transfer calli to fresh the 2nd selection media (A-6), wrap in 3M Micropore tape and incubate in the dark at 27° C. for 2 weeks. Firmly place the callus on the media—do not embed into the media. Be careful to group and mark the calli pieces that came from the same embryo.

5.1 Improved Selection Protocol

Alternatively and preferably an improved selection scheme is applied: All methods (including the basic method described above) disclosed for maize transformation in the art require 2 to 3 transfers to selection media with the same or different concentrations of selection reagent. A transfer means to move callus materials from current media plates to a set of new media plates. The transfer process is labor intensive and time consuming e.g., it takes 60 min to transfer callus materials derived from 100 immature embryos. In the improved, simplified method of the invention, only one transfer to selection medium is required. In consequence, about 30% of time and labor (i.e., 60 min for every 100 immature embryos-derived materials) is saved.

While the basic requires growing callus on selection media for usually 5 to 6 weeks, the improved, simplified method requires 4 weeks. Thus, the whole transformation process is shortened by 1 to 2 weeks.

It showed that it is possible to produce transgenic events with the improved, simplified method in BPS553×(HiIIA× A188) genotype with either 0.5 µM or 0.75 µM PURSUIT™ and in HiIIA×A188 genotype with only 0.5 µM PURSUIT™ at callus stage for selection. Transformation efficiency averaged 20.5% for BPS553×(HiIIA×A188) genotype and 2.5 for HiIIA×A188 genotype. In comparison to the standard transformation protocol (2 weeks on medium with 0.5 µM PURSUIT™ followed by another 3 weeks on medium containing 0.75 µM PURSUIT™ for another three weeks) the simplified method had a transformation efficiency of 36.7% while the former method had an efficiency of 33.3%. Thus transformation efficiencies were comparable for both methods.

TABLE 4

Comparison of old and improved simplified methods

| Method | Genotype | Cob # | # IE | # plants regenerate | # PCR + plants | TE (%) |
|---|---|---|---|---|---|---|
| Old | BPS553x(HxA) | 1 | 60 | 20 | 20 | 33.3 |
| Simplified | BPS553x(HxA) | 1 | 60 | 22 | 22 | 36.7 |
| | Total | | 120 | 42 | 42 | 35.0 |

BPS553x(HxA): BPS553 x(HillAxA188)
\# IE = number of immature embryos used for transformation.
TE: Transformation efficiency (%) = number of PCR + plants/# IE × 100

More specifically the improved selection protocol is carried out as follows: Looking through a dissecting microscope and using a pair of forceps to remove embryos axis, pick and transfer immature embryos with callus cells that are actively growing to fresh M-LS-401 medium in 25×100 mm plates, for some genotype M-LS-301 medium can be used as well. Plate only 8-10 embryos per plate. Make sure all embryos touch the surface of the medium. Seal the plates with porous tape. Grow the material at 25° C. in the dark for 25 to 28 days. Preferably, do not let them grow for more than 4 weeks on callus selection medium. Select callus materials that are actively growing under a dissecting microscope and transfer to regeneration medium as described below.

Example 6

Regeneration of Transformed Plants 6.1 Basic Regeneration Protocol

Excise the proliferated calli (whitish with embryonic structures forming), in the same manner as for $2^{nd}$ selection and transfer to regeneration media (A-7) in 25×100 mm plates. Firmly place the callus on the media—do not embed into the media. Wrap the plates in 3M Micropore tape and put in the light at 25 or 27° C. Be careful to group the calli pieces that came from the same embryo and number them by embryo.

Incubate under light (ca. 2,000 lux; 14/10 hr light/dark) at 25 or 27° C. for 2 to 3 weeks, or until shoot-like structures are visible. Transfer to fresh regeneration media if necessary. Transfer calli sections with regenerated shoots or shoot-like structures to a Phytatray or Magenta boxes containing rooting medium (A-8) and incubate for 2 weeks under the same condition for the above step, or until rooted plantlets have developed. After 2 to 4 weeks on rooting media, transfer calli that still have green regions (but which have not regenerated seedlings) to fresh rooting Phytatrays. Seedling samples are taken for TaqMan analysis to determine the T-DNA insertion numbers.

Transfer rooted seedlings to Metromix soil in greenhouse and cover each with plastic dome for at least 1 week, until seedlings have established. Maintain the plants with daily watering, and supplementing liquid fertilizer twice a week. When plants reach the 3 to 4 leaf-stages, they are fertilized with Osmocote. If needed putative transgenic plants are sprayed with 70 to 100 g/ha Pursuit™ by a licensed person, and grown in the greenhouse for another two weeks. Non-transgenic plants should develop herbicidal symptoms or die in this time. Survived plants are transplanted into 10" pots with MetroMix and 1 teaspoon Osmocote™.

At the flowering stage, the tassels of transgenic plants are bagged with brown paper bags to prevent pollen escape. Pollination is performed on the transgenic plants. It is best to do self-pollination on the transgenic plants. If silking and anthesis are not synchronized, a wild-type pollen donor or recipient plant with same genetic background as the transgenic $T_0$ plant should be available for performing cross-pollination. $T_1$ seeds are harvested, dried and stored properly with adequate label on the seed bag. After harvesting the transgenic $T_1$ seeds, $T_0$ plants including the soil and pot should be bagged in autoclave bags and autoclaved (double bagging).

6.2 Improved Regeneration Protocol

In a preferred embodiment of the invention an improved procedure is employed. The basic protocol and the transformation protocols known in the art regenerate transgenic plants on plates, then transferred to a box containing medium to stimulate rooting. Rooted planted are later transplanted to MetroMix in the greenhouse. This procedure is labor intensive and time consuming. In the improved method, plantlets regenerated on plates are directly transplanted to MetroMix in the greenhouse, omitting the step in the rooting box, thereby saving time and labor.

Thus, more specifically callus materials are selected that are actively growing under a dissecting microscope and transfer to M-LS-503 or M-LS-504 medium in 25×100 mm plates. Keep plates in culture room set at 14/10 hr light/dark and 25° C. and grow for 2 to 3 weeks till shoot regenerates. Transplant healthy and vigorously growing shoots to pots with Metro Mix in the greenhouse. From here on follow the greenhouse protocol as described above. At least 50% of the shoots survive the transplanting process. The result showed that two separate experiments had survival rate of 62 and 93%, respectively.

Example 7

Comparison of Transformation Efficiencies for Maize Hybrids

Immature embryos were derived from maize hybrid lines (as specified in Table 5 below) and transformed by *Agrobacterium* mediated transformation as described above. Transgenic events were confirmed with TaqMan™ analysis.

TABLE 5

Transformation efficiency for two different hybrid sources for immature embryos

| Hybrid as source for immature embryo | # immature embryos infected | # Independent transgenic events produced | Transformation efficiency [%] |
| --- | --- | --- | --- |
| HillAxA188 | 588 | 60 | 10.2 |
| BPS553x (HillAxA188) | 156 | 33 | 21.2 |

For BPS553x(HiIIAxA188) genotypes, the transformation efficiency is high enough, that the addition of silver nitrate and L-cysteine to the co-cultivation medium can be omitted. However, addition of these compounds further enhances transformation efficiency.

In order to demonstrating the transformability of F2 generation of hybrid BPS553x(HiIIAx188), F1 plants of BPS553x(HiIIAxA188) were self-pollinated, and the F2 immature embryos were transformed based on the protocol without using L-cysteine in the co-cultivation medium, as described in this application. Similar transformation efficiencies were obtained with both F1 and F2 immature embryos (Table 6).

TABLE 6

Transformation comparison of F1 and F2 generations of BPS553 x (HillAxA188) hybrid lines. F2 immature embryos were produced by self-pollinating F1 plants of BPS553 x (HillAxA188). Transformation experiments were conducted without applying L-cysteine in the co-cultivation medium.

| Generation | Number of replicates | Total number of immature embryos infected | Number of confirmed events | Transformation efficiency (%) |
| --- | --- | --- | --- | --- |
| F1 | 4 | 442 | 54 | 12.2 |
| F2 | 4 | 380 | 43 | 11.3 |

REFERENCES

The references listed below and all references cited herein are incorporated herein by reference to the extent that they supplement, explain, provide a background for, or teach methodology, techniques, and/or compositions employed herein.

1. An et al. (1985) EMBO J 4:277-287
2. Anderson & Gregeson (1989) Genome 31:994-999
3. Ashby et al. (1988) J. Bacteriol. 170: 4181-4187
4. Atanassova et al. (1992) Plant J 2(3): 291-300
5. Ausubel F M et al. (1987) Current Protocols in Molecular Biology, Greene Publishing Assoc. and Wiley Interscience
6. Baker et al. (1987) EMBO J 6: 1547-1554
7. Bäumlein et al. (1992) Plant J 2(2):233-9;
8. Bäumlein H et al. (1991a) Mol Gen Genet 225(3):459-467
9. Bäumlein H et al. (1991b) Mol Gen Genet 225:121-128
10. Becker et al. (1994) Plant J., 5:299-307,
11. Benfey et al. (1989) EMBO J 8:2195-2202
12. Bernasconi P et al. (1995) J. Biol. Chem. 270(29):17381-17385
13. Bevan et al., (1984) Nucl Acid Res 12, 8711-4720
14. Bolton et al. (1986) Science 232: 983-985;
15. Bruce et al. (1989) Proc Natl Acad Sci USA 86:9692-9696
16. Bustos M M et al. (1989) Plant Cell 1(9):839-53)
17. Chen and Winans (1991) J. Bacteriol. 173: 1139-1144
18. Christensen et al. (1989) Plant Mol. Biol. 12: 619-632
19. Christensen et al. (1992) Plant Mol Biol 18:675-689
20. Christou et al. (1988) Plant Physiol 87:671-674
21. Christou et al. (1991) Bio/Technology 9:957-962
22. Chui W L et al., (1996) Curr Biol 6:325-330;
23. Currie et al. (1995) Weed Sci. 43:578-582
24. Dale & Ow (1991) Proc Nat'l Acad Sci USA 88:10558-10562
25. Datta et al. (1990b) Bio/Technology 8:736-740
26. Davey et al. (1991) J Exp Bot 42:1129-1169
27. de Block et al., (1987) EMBO J 6:2513-2518
28. de Bruijn et al. (1996) Rep-PCR Genomic Fingerprinting of Plant-Associated Bacteria and Computer-Assisted Phylogenetic Analyses In: Biology of Plant-Microbe Interaction; Proceedings of the 8th International Congress of Molecular Plant-Microbe Interactions (G. Stacey, B. Mullin and P. Gresshoff, Eds.) APS Press, 497-502
29. De la Pena et al. (1987) Nature 325:274-276
30. Deblaere et al. (1985) Nucl Acids Res 13:4777-4788
31. Della-Cioppa et al. (1987) Bio/Technology 5:579-584
32. Dellaporta et al. (1988) In: Chromosome Structure and Function: Impact of New Concepts, 18th Stadler Genetics Symposium, 11:263-282
33. Du et al. (1989) Genet Manip Plants 5:8-12
34. Dunwell J M (2000) J Exp Bot 51 Spec No:487-96
35. Ebinuma et al. (2000a) Proc Natl Acad Sci USA 94:2117-2121
36. Ebinuma et al. (2000b) Selection of Marker-free transgenic plants using the oncogenes (ipt, rol A, B, C) of *Agrobacterium* as selectable markers, In Molecular Biology of Woody Plants. Kluwer Academic Publishers
37. Eichholtz et al. (1987) Somatic Cell and Molecular Genetics 13, 67-76
38. EP-A1 0 120 516
39. EP-A1 0 333 033
40. EP-A1 0 335 528
41. EP-A1 0 388 186
42. EP-A1 0 601 092
43. EP-A1 0 672 752
44. EP-A1 0 709 462
45. EP-A1 0 807 836

46. Erikson et al. (2004) Nat Biotechnol. 22(4):455-8
47. Farrand et al. (2003) Int. J. Systematic & Evolutionary Microbiology 53:1681-1687
48. Fedoroff N V & Smith D L (1993) Plant J 3:273-289
49. Fire A. et al (1998) Nature 391:806-811
50. Fraley et al. (1983) Proc Natl Acad Sci USA 80:4803
51. Frame et al. (2002) Plant Physiol. 129: 13-22
52. Franck et al., (1980) Cell 21:285-294
53. Fromm et al. (1986) Nature 319:791-793
54. Fromm et al. (1990) Bio/Technology 8:833-839
55. Gallie et al. (1987) Nucl Acids Res 15:8693-8711
56. Gardner et al. (1986) Plant Mol Biol 6:221-228
57. Gatz et al. (1991) Mol Gen Genetics 227:229-237
58. Gatz et al. (1992) Plant J 2:397-404
59. Gatz et al. (1994) Mol Gen Genetics 243:32-38
60. Gatz et al., (1997) Annu Rev Plant Physiol Plant Mol Biol 48:89-108
61. Gelvin et al. (Eds) (1990) Plant Molecular Biology Manual; Kluwer Academic Publisher, Dordrecht, The Netherlands
62. Gleave A P et al. (1999) Plant Mol Biol. 40(2):223-35
63. Gordon-Kamm et al. (1990) Plant Cell 2:603-618
64. Gould et at. (1991) Plant Physiol 95(2):426-434
65. Gruber et al. (1993) "Vectors for Plant Transformation," in METHODS IN PLANT MOLECULAR BIOLOGY AND BIOTECHNOLOGY; pp. 89-119.
66. Guerrero et al. (1993) Mol Gen Genet. 224:161-168
67. Guivarc'h et al. (1993) Protoplasma 174:10-18
68. Hajdukiewicz et al. (1994) Plant Mol Biol 25:989-994
69. Hansen et al. (1994) Proc. Natl. Acad. Sci. USA 91:7603-7607
70. Haseloff et al. (1997) Proc Natl Acad Sci USA 94(6): 2122-2127
71. Hayakawa et al. (1992) Proc Natl Acad Sci USA 89:9865-9869
72. Hayford et al. (1988) Plant Physiol. 86:1216
73. Hershey et al. (1991) Mol Gen Genetics 227:229-237
74. Hiei et al. (1994) Plant J 6: 271-282
75. Hille et al., (1986) Plant Mol. Biol. 7:171
76. Hoekema (1985) In: The Binary Plant Vector System, Offsetdrukkerij Kanters B. V., Alblasserdam, Chapter V
77. Hoekema et al. (1983) Nature 303:179-181
78. Holsters et al. (1978) Mol Gen Genet 163:181-187
79. Holtorf S et al. (1995) Plant Mol Biol 29:637-649
80. Hood et al. (1986) J Bacteriol 168:1291-1301
81. Hooykaas P J J et al. (1977) J Gen Microbiol 98:477-484
82. Horsch R B et al. (1985) Science 225: 1229f
83. Ishida Y et al., (1996) Nature Biotech 745-750
84. Jacq et al. (1993) Plant Cell Reports 12: 621-624
85. James et al. (1993) Plant Cell Reports 12: 559-563
86. Jarchow et al. (1991), Proc. Natl. Acad. Sci. USA 88:10426-10430
87. Jefferson (1987b) Plant Mol. Bio. Rep., 5:387-405
88. Jefferson et al. (1987a) EMBO J., 6:3901-3907
89. Jenes B et al. (1993) Techniques for Gene Transfer, in: Recombinant Plants, Vol. 1, Engineering and Utilization, edited by S D Kung and R Wu, Academic Press, pp. 128-143
90. Jones et al. (1987) Mol. Gen. Genet., 210:86
91. Joseffson L G et al. (1987) J Biol Chem 262:12196-12201
92. Kado (1991) Crit Rev Plant Sci 10:1
93. Klapwijk et al. (1980) J. Bacteriol., 141, 128-136
94. Klein & Klein (1953) J Bacteriol. 66 (2): 220-228;
95. Koncz & Schell (1986) Mol Gen Genet 204:383-396
96. Koprek T et al. (1999) Plant J 19(6): 719-726
97. Last D I et al. (1991) Theor. Appl. Genet. 81, 581-588
98. Lawson et al. (1994) Mol Gen Genet 245:608-615
99. Leffel S M et al. (1997) Biotechniques. 23(5):912-8
100. Lepetit et al. (1992) Mol. Gen. Genet. 231: 276-285
101. Li et al. (1992) Plant Mol Biol 20:1037-1048
102. Llob et al. (2003) Europ J Plant Pathol 109:381-389
103. Ludwig et al. (1990) Science 247:449
104. Luo and Wu (1988) Plant Mol. Biol. Rep. 6:165-174
105. Lysnik et al. (1993) NAR 21:969-975
106. Maniatis T, Fritsch E F and Sambrook J (1989) Molecular Cloning: A Laboratory Manual, 2nd Ed., Cold Spring Harbor Laboratory, Cold Spring Harbor (N.Y.)
107. Matzke M A et al. (2000) Plant Mol Biol 43:401-415
108. McElroy et al., Plant Cell 2: 163171 (1990)
109. Mett et al. PNAS 90: 4567-4571 (1993)
110. Miki et al. (1993) "Procedures for Introducing Foreign DNA into Plants" in METHODS IN PLANT MOLECULAR BIOLOGY AND BIOTECHNOLOGY; pp. 67-88
111. Millar et al., (1992) Plant Mol Biol Rep 10:324-414
112. Mogensen H L (1982) Carlsberg Res. Commun. 47, 313-354.
113. Mol J N et al. (1990) FEBS Lett 268(2):427-430
114. Moloney et al. (1989) Plant Cell Reports 8: 238
115. Mooney and Doodwin (1991) Plant Cell Tissue Organ Culture 25:209-218
116. Mozo & Hooykaas (1991) Plant Mol. Biol. 16:917-918
117. Murai et al., (1983) Science 23: 476-482
118. Murashige T and Skoog F (1962) Physiol. Plant. 15, 472-497
119. Naested H (1999) Plant J 18:571-576
120. Nehra et al. (1994) Plant J. 5:285-297
121. Newhouse et al. (1991) Theor Appl Gene. 83:65-70.
122. Odell et al. (1990) Mol Gen Genet 223:369-378
123. Olhoft P M et al. (2001) Plant Cell Rep 20: 706-711
124. Ow et al. (1986) Science 234:856-859;
125. Paszkowski et al. (1984) EMBO J 3:2717-2722
126. Perera R J et al. (1993) Plant Mol. Biol 23(4): 793-799
127. Perl A et al. (1996) Nature Biotechnol 14: 624-628
128. Potrykus (1990) Bio/technology. 8, 535-542.
129. Potrykus (1991) Ann Rev Plant Physiol Plant Mol Biol 42:205-225
130. Prasher et al. (1985) Biochem Biophys Res Commun 126(3):1259-1268
131. Raineri et al. (1990) Bio/Technology 8:33
132. Rasco-Gaunt et al. (2001) J. Exp. Bot. 52: 865-874
133. Reichel et al. (1996) Proc Natl Acad Sci USA 93(12): 5888-5893
134. Rhodes C A et al. (1988) Science 240, 204-207
135. Rouster J et al. (1998) Plant J 15:435-440
136. Sanford J C (1990) Physiologia Plantarium 79:206-209
137. Sauer B (1998) Methods 14(4):381-92
138. Sautter et al. (1991) Bio/Technology, 9:1080-1085
139. Sawada et al. (1993) International Journal of Systematic Bacteriology 43(4):694-702
140. Scheeren-Groot et al. (1994) J. Bacteriol 176: 6418-6426
141. Schena et al. (1991) Proc Nat'l Acad Sci USA 88:10421
142. Schenborn E, Groskreutz D. (1999) Mol Biotechnol 13(1):29-44
143. Schlaman H R M and Hooykaas P J J (1997) Plant J 11:1377-1385
144. Sengupta-Gopalan et al. (1985) Proc. Nat'l. Acad. Sci. USA 82: 3320-3324
145. Shah et al. (1986) Science 233: 478
146. Sheehy et al. (1988) Proc Natl Acad Sci USA 85: 8805-8809;
147. Sheen et al. (1995) Plant J 8(5):777-784;
148. Shewmaker et al. (1985) Virology 140:281-288
149. Shillito et al. (1985) Bio/Technology, 3:1099-1103

150. Shimamoto et al. (1989) Nature 338:274-276
151. Shirsat A et al. (1989) Mol Gen Genet 215(2):326-331
152. Silhavy T J, Berman M L and Enquist L W (1984) Experiments with Gene Fusions, Cold Spring Harbor Laboratory, Cold Spring Harbor (N.Y.)
153. Simpson et al. (1985) EMBO J 4:2723-2729
154. Somers et al. (1992) Bio/Technology 10:1589-1594
155. Stachel et al. (1985) Nature 318: 624-629
156. Stalberg K et al. (1996) Planta 199:515-519
157. Stougaard J (1993) Plant J 3:755-761
158. Sundaresan et al. (1995) Gene Develop 9: 1797-1810
159. Suzuki (2001) Gene. January 24; 263(1-2):49-58
160. Svab et al., (1990) Plant Mol. Biol. 14:197
161. The Maize Handbook, Chapter 116, Freeling and Walbot, Eds., Springer, N.Y. (1994)
162. Tian et al. (1997) Plant Cell Rep 16:267-271;
163. Timko et al., (1985) Nature 318: 579-582
164. Topfer et al. (1989) Plant Cell, 1:133-139
165. Twell et al. (1983) Sex. Plant Reprod. 6: 217-224
166. Twell et al. (1989b) Mol Gen Genet 217:240-245
167. U.S. Pat. No. 4,761,373
168. U.S. Pat. No. 4,801,340;
169. U.S. Pat. No. 4,962,028
170. U.S. Pat. No. 4,975,374)
171. U.S. Pat. No. 4,940,838
172. U.S. Pat. No. 5,225,341
173. U.S. Pat. No. 5,304,732
174. U.S. Pat. No. 5,352,605
175. U.S. Pat. No. 5,504,200
176. U.S. Pat. No. 5,565,350
177. U.S. Pat. No. 5,608,152;
178. U.S. Pat. No. 5,683,439
179. Van Laerebeke et al. (1974) Nature 252, 169-170
180. van Veen R J M et al. (1988) Mol Plant Microb Interact 1(6):231-234
181. Van Wordragen and Dons (1992) Plant Mol. Biol. Rep. 10: 12-36
182. Vanden Elzen et al. (1985) Plant Mol Biol. 5:299
183. Vasil et al. (1992) Bio/Technology, 10:667-674
184. Vasil et al. (1993) Bio/Technology, 11:1153-1158
185. Velten J et al. (1984) EMBO J. 3(12): 2723-2730.
186. Vernade et al. (1988) J. Bacteriol. 170: 5822-5829
187. Vinuesa et al. (1998) Appl. Envir. Microbiol. 64:2096-2104
188. Wader et al., in TOMATO TECHNOLOGY 189-198 (Alan R. Liss, Inc. 1987)
189. Wan & Lemaux (1994) Plant Physiol., 104:3748
190. Ward et al. (1993) Plant Mol Biol 22:361-366
191. Waterhouse P M et al. (1998) Proc Natl Acad Sci USA 95:13959-64
192. Watson et al. (1975) J. Bacteriol 123, 255-264
193. Watson et al. (1985) EMBO J 4(2):277-284
194. Weeks et al. (1993) Plant Physiol 102:1077-1084
195. WO 00/15815
196. WO 00/26388
197. WO 00/58484
198. WO 00/63398
199. WO 03/060133
200. WO 84/02913
201. WO 91/13980
202. WO 91/13991
203. WO 93/01294
204. WO 93/18168
205. WO 93/21334
206. WO 94/00583
207. WO 94/00977
208. WO 95/06722
209. WO 95/15389
210. WO 95/19443
211. WO 95/23230
212. WO 97/41228
213. WO 98/45456
214. WO 99/16890
215. WO 00/44895
216. WO 00/44914
217. WO 00/49035
218. WO 00/63364
219. WO 00/68374
220. WO 99/32619
221. WO 99/53050
222. Young et al. (2003) Int. J. Systematic & Evolutionary Microbiology 51:89-103
223. Zupan et al. (2000) Plant J 23(1):11-28

The invention claimed is:

1. A method for generating a transgenic *Zea mays* plant, comprising the steps of:
    a. isolating an immature embryo of a *Zea mays* plant,
    b. co-cultivating said isolated immature embryo with a bacterium belonging to the genus Rhizobiaceae comprising at least one transgenic T-DNA, said T-DNA comprising at least one selectable marker gene, with a co-cultivation medium comprising silver nitrate and L-Cysteine, wherein the isolated immature embryos are placed on one or more layers of filter paper on the surface of agar co-cultivation medium, or on one or more layers of filter paper containing liquid co-cultivation medium solution in a plate without agar medium,
    c. transferring the co-cultivated immature embryo to a recovering medium comprising:
        i. an effective amount of at least one antibiotic that inhibits or suppresses the growth of the bacterium belonging to the genus Rhizobiaceae,
        ii. L-proline in a concentration from about 1 g/l to about 10 g/l,
        iii. silver nitrate in a concentration from about 1 μM to about 50 μM, and
        iv. an effective amount of at least one auxin compound, but not comprising an effective amount of a phytotoxic selection agent,
    d. inducing formation of embryogenic callus and selecting a transgenic callus on a medium comprising:
        i. an effective amount of at least one auxin compound, and
        ii. an effective amount of a selection agent allowing for selection of callus comprising the at least one transgenic T-DNA, and
    e. regenerating and selecting plants containing the at least one transgenic T-DNA from said transgenic callus 2. The method of claim 1, wherein said immature embryo is isolated from the group consisting of inbreds, hybrids, F1 between inbreds, F1 between an inbred and a hybrid, F1 between an inbred and a naturally-pollinated variety, commercial F1 varieties, any F2 crossing or self-pollination between the before mentioned varieties, and the progeny of any of the before mentioned.

3. The method of claim 1, wherein the immature embryo is isolated from a cross of a (HiIIA×A188) hybrid with an inbred-line selected from the group of which representative seed having been deposited with the American Type Culture Collection under the Patent Deposit Designation PTA-6170 and PTA-6171.

4. The method of claim 1, wherein said immature embryo is one in the stage of not less than 2 days after pollination.

5. The method of claim 1, wherein the immature embryos are isolated and directly inoculated with a suspension of the Rhizobiaceae bacterium without additional washing steps.

6. The method of claim 1, wherein the auxin compound is a combination of 2,4-D and Picloram.

7. The method of claim 1, wherein said immature embryo is treated with an enzyme or is injured.

8. The method of claim 1, wherein the co-cultivation medium comprises from about 1 μM to about 10 μM of silver nitrate and from about 50 mg/L to about 1,000 mg/L of L-Cysteine.

9. The method of claim 1, wherein the selection is carried out in a single selection step without intermediate tissue transfer.

10. The method of claim 1, wherein rooted plantlets resulting from the regeneration step are directly transferred into soil medium.

11. A transgenic maize plant generated from the method of claim 3.

12. A part of the maize plant of claim 11.

13. The method of claim 1, wherein the isolated immature embryo has not been subjected to a dedifferentiation treatment.

14. The method of claim 1, wherein the co-cultivation medium comprises from about 1 μM to about 10 μM of silver nitrate.

15. The method of claim 1, wherein the co-cultivation medium comprises 15 μM of silver nitrate.

16. The method of claim 1, wherein the co-cultivation medium comprises from about 50 mg/L to about 1,000 mg/L of L-Cysteine.

17. The method of claim 1, wherein the co-cultivation medium comprises from about 1 mM to about 10 mM of L-Cysteine.

* * * * *

SEQUENCE LISTING

```
<160> NUMBER OF SEQ ID NOS: 3

<210> SEQ ID NO 1
<211> LENGTH: 15997
<212> TYPE: DNA
<213> ORGANISM: Unknown
<220> FEATURE:
<223> OTHER INFORMATION: Vector pBPSMM232
<220> FEATURE:
<221> NAME/KEY: misc_feature
<222> LOCATION: (2305)..(4305)
<223> OTHER INFORMATION: coding for glucuronidase (GUS) gene (plus
      intron)
<220> FEATURE:
<221> NAME/KEY: promoter
<222> LOCATION: (298)..(2278)
<223> OTHER INFORMATION: maize ubiquitin promoter
<220> FEATURE:
<221> NAME/KEY: misc_feature
<222> LOCATION: (6141)..(8057)
<223> OTHER INFORMATION: complement: mutated maize AHAS selection marker
      gene
<220> FEATURE:
<221> NAME/KEY: misc_feature
```

```
<222> LOCATION: (148)..(172)
<223> OTHER INFORMATION: complement: left T-DNA border
<220> FEATURE:
<221> NAME/KEY: misc_feature
<222> LOCATION: (10103)..(10126)
<223> OTHER INFORMATION: complement: right T-DNA border
<220> FEATURE:
<221> NAME/KEY: rep_origin
<222> LOCATION: (12490)..(12770)
<223> OTHER INFORMATION: pBR322 origin of replication
<220> FEATURE:
<221> NAME/KEY: rep_origin
<222> LOCATION: (12489)..(13170)
<223> OTHER INFORMATION: ColE1 origin of replication
<220> FEATURE:
<221> NAME/KEY: terminator
<222> LOCATION: (4925)..(6140)
<223> OTHER INFORMATION: complement: maize AHAS terminator

<400> SEQUENCE: 1
cgttcttccg aatagcatcg gtaacatgag caaagtctgc cgccttacaa cggctctccc     60
gctgacgccg tcccggactg atgggctgcc tgtatcgagt ggtgattttg tgccgagctg    120
ccggtcgggg agctgttggc tggctggtgg caggatatat tgtggtgtaa acaaattgac    180
gcttagacaa cttaataaca cattgcggac gttttttaatg tactgaattg actagtggcg    240
cgccaagctt gcatgcctgc aggtcgactc tagaggatcc ccatcgaatt cctgcagtgc    300
agcgtgaccc ggtcgtgccc ctctctagag ataatgagca ttgcatgtct aagttataaa    360
aaattaccac atatttttt tgtcacactt gtttgaagtg cagtttatct atctttatac    420
atatatttaa actttactct acgaataata taatctatag tactacaata atatcagtgt    480
tttagagaat catataaatg aacagttaga catggtctaa aggacaattg agtattttga    540
caacaggact ctacagtttt atcttttag tgtgcatgtg ttctcctttt tttttgcaaa    600
tagcttcacc tatataatac ttcatccatt ttattagtac atccatttag ggtttagggt    660
taatggtttt tatagactaa ttttttttagt acatctattt tattctattt tagcctctaa    720
attaagaaaa ctaaaactct attttagttt ttttatttaa taatttagat ataaaataga    780
ataaaataaa gtgactaaaa attaaacaaa tacccttaa gaaattaaaa aaactaagga    840
aacatttttc ttgtttcgag tagataatgc cagcctgtta aacgccgtcg acgagtctaa    900
cggacaccaa ccagcgaacc agcagcgtcg cgtcgggcca agcgaagcag acggcacggc    960
atctctgtcg ctgcctctgg acccctctcg agagttccgc tccaccgttg gacttgctcc   1020
gctgtcggca tccagaaatt gcgtggcgga gcggcagacg tgagccggca cggcaggcgg   1080
cctcctcctc ctctcacggc accggcagct acggggatt cctttcccac cgctccttcg   1140
ctttcccttc ctcgcccgcc gtaataaata gacacccct ccacccctc tttcccaac    1200 ctcgtgttgt tcggagcgca cacacacaca accagatctc ccccaaatcc accgtcggc   1260 acctccgctt caaggtacgc cgctcgtcct cccccccccc cctctctac cttctctaga   1320 tcggcgttcc ggtccatggt tagggcccgg tagttctact tctgttcatg tttgtgttag   1380
atccgtgttt gtgttagatc cgtgctgcta gcgttcgtac acggatgcga cctgtacgtc   1440
agacacgttc tgattgctaa cttgccagtg tttctctttg gggaatcctg ggatggctct   1500
agccgttccg cagacgggat cgatttcatg atttttttg tttcgttgca tagggttgg    1560 tttgcccttt tcctttattt caatatatgc cgtgcacttg tttgtcgggt catcttttca   1620 tgctttttt tgtcttggtt gtgatgatgt ggtctggttg ggcggtcgtt ctagatcgga   1680
gtagaattct gtttcaaact acctggtgga tttattaatt ttggatctgt atgtgtgtgc   1740
catacatatt catagttacg aattgaagat gatggatgga aatatcgatc taggataggt   1800
```

```
atacatgttg atgcgggttt tactgatgca tatacagaga tgcttttgt tcgcttggtt      1860 gtgatgatgt ggtgtggttg ggcggtcgtt cattcgttct agatcggagt agaatactgt    1920
ttcaaactac ctggtgtatt tattaatttt ggaactgtat gtgtgtgtca tacatcttca    1980
tagttacgag tttaagatgg atggaaatat cgatctagga taggtataca tgttgatgtg    2040
ggttttactg atgcatatac atgatggcat atgcagcatc tattcatatg ctctaacctt    2100
gagtacctat ctattataat aaacaagtat gttttataat tattttgatc ttgatatact    2160
tggatgatgg catatgcagc agctatatgt ggattttttt agccctgcct tcatacgcta    2220
tttatttgct tggtactgtt tcttttgtcg atgctcaccc tgttgtttgg tgttacttct    2280
gcagcccggg taggtcagtc ccttatgtta cgtcctgtag aaaccccaac ccgtgaaatc    2340
aaaaaactcg acggcctgtg ggcattcagt ctggatcgcg aaaactgtgg aattggtcag    2400
cgttggtggg aaagcgcgtt acaagaaagc cgggcaattg ctgtgccagg cagttttaac    2460
gatcagttcg ccgatgcaga tattcgtaat tatgcgggca acgtctggta tcagcgcgaa    2520
gtctttatac cgaaaggttg gcaggccag cgtatcgtgc tgcgtttcga tgcggtcact    2580
cattacggca aagtgtgggt caataatcag gaagtgatgg agcatcaggg cggctatacg    2640
ccatttgaag ccgatgtcac gccgtatgtt attgccggga aaagtgtacg taagtttctg    2700
cttctacctt tgatatatat ataataatta tcattaatta gtagtaatat aatatttcaa    2760 atatttttt caaaataaaa gaatgtagta tatagcaatt gcttttctgt agtttataag    2820
tgtgtatatt ttaatttata acttttctaa tatatgacca aaatttgttg atgtgcaggt    2880
atcaccgttt gtgtgaacaa cgaactgaac tggcagacta tcccgccggg aatggtgatt    2940
accgacgaaa acggcaagaa aaagcagtct tacttccatg atttctttaa ctatgccgga    3000
atccatcgca gcgtaatgct ctacaccacg ccgaacacct gggtggacga tatcaccgtg    3060
gtgacgcatg tcgcgcaaga ctgtaaccac cgcgtctgttg actggcaggt ggtggccaat    3120
ggtgatgtca gcgttgaact gcgtgatgcg gatcaacagg tggttgcaac tggacaaggc    3180
actagcggga ctttgcaagt ggtgaatccg cacctctggc aaccgggtga aggttatctc    3240
tatgaactgt gcgtcacagc caaaagccag acagagtgtg atatctaccc gcttcgcgtc    3300 ggcatccgt cagtggcagt gaagggcgaa cagttcctga ttaaccacaa accgttctac    3360
tttactggct ttggtcgtca tgaagatcgc gacttgcgtg gcaaaggatt cgataacgtg    3420
ctgatggtgc acgaccacgc attaatggac tggattgggg ccaactccta ccgtacctcg    3480
cattaccctt acgctgaaga gatgctcgac tgggcagatg aacatggcat cgtggtgatt    3540
gatgaaactg ctgctgtcgg ctttaacctc tctttaggca ttggtttcga agcgggcaac    3600
aagccgaaag aactgtacag cgaagaggca gtcaacgggg aaactcagca agcgcactta    3660
caggcgatta aagagctgat agcgcgtgac aaaaaccacc caagcgtggt gatgtggagt    3720
attgccaacg aaccggatac ccgtccgcaa ggtgcacggg aatatttcgc gccactggcg    3780
gaagcaacgc gtaaactcga cccgacgcgt ccgatcacct gcgtcaatgt aatgttctgc    3840
gacgctcaca ccgataccat cagcgatctc tttgatgtgc tgtgcctgaa ccgttattac    3900
ggatggtatg tccaaagcgg cgatttggaa acggcagaga aggtactgga aaaagaactt    3960
ctggcctggc aggagaaact gcatcagccg attatcatca ccgaatacgg cgtggatacg    4020
ttagccgggc tgcactcaat gtacaccgac atgtggagtg aagagtatca gtgtgcatgg    4080
ctggatatgt atcaccgcgt ctttgatcgc gtcagcgccg tcgtcggtga acaggtatgg    4140
aatttcgccg attttgcgac ctcgcaaggc atattgcgcg ttggcggtaa caagaaaggg    4200
```

```
atcttcactc gcgaccgcaa accgaagtcg gcggcttttc tgctgcaaaa acgctggact    4260
ggcatgaact tcggtgaaaa accgcagcag ggaggcaaac aatgaatcaa caactctcct    4320
ggcgcaccat cgtcggctac agcctcggga attgctaccg agctcgaatt tccccgatcg    4380
ttcaaacatt tggcaataaa gtttcttaag attgaatcct gttgccggtc ttgcgatgat    4440
tatcatataa tttctgttga attacgttaa gcatgtaata attaacatgt aatgcatgac    4500
gttatttatg agatgggttt ttatgattag agtcccgcaa ttatacattt aatacgcgat    4560
agaaaacaaa atatagcgcg caaactagga taaattatcg cgcgcggtgt catctatgtt    4620
actagatcgg gaattggcat gcaagcttgg cactggccgt cgttttacaa cgtcgtgact    4680
gggaaaaccc tggcgttacc caacttaatc gccttgcagc acatcccct ttcgccagct    4740 ggcgtaatag cgaagaggcc cgcaccgatc gcccttccca acagttgcgc agcctgaatg    4800
gcgaatgcta gcagcttg agcttggatc agattgtcgt ttcccgcctt cagtttgtgt    4860
taattaacgg tccgaggcct cctcagcaag ctgttaacgc gatcgcagcg ccttaagggg    4920
ccgctctaga ttagtgtacg gaataaaagt cctaattcat tcttttctt atacgtcacc    4980 gttttctaca tttagaaaaa tgaagtggga atcaattgaa acaattgata gctttaaata    5040
tcaagctgtc ttctccagga ccaggcccca gcacatcggc gtggaaagcg ctaggcccca    5100
gaacaactcg tcaatcgtca tggcaaataa tgacacattg agccgatttg atgcatggaa    5160
cagactaata aggaactcaa atctctttgg agattgaatg attgagatga aaatgaatta    5220 atatttttc tcaatcccct ccaatgctaa gaaagtttga gttccaaat tagctttaga    5280 gggcgtttag atcccttcgt tttagagaaa ttagaattca ctcaataaaa taacttattt    5340
aatttggaat ttgatattca accacttttc aaagtttaga tataggtcta tctcaaattc    5400
atagggtgga tgatggaaat gattttatgc attaatagaa tttgtttcta ctgtgtaact    5460
tacatgacac tcttcatctc actcctgtat agtaaaaatg tagcatataa atatctccga    5520
catcttgata ataatagtat acaaatatat tttgcataaa accgaattaa cttaattgat    5580
atatgccaaa attactatta ttagaatgga atttaattcc aatgatccaa accacgaaaa    5640
tggatcaggt aactaattca gtcaaatgcc tcattttttt tcactcccct caaaccacga    5700
aaatgccatt ctggtttgta aaatagtttg aaattgcagc cctagcatta ttccatacat    5760
catatgttga gttgaaatta ccaatataat aataactaaa aaaggaaaaa aatagcgaaa    5820
acaaaagcaa ggaccagttg gacacttaaa tttggcaaca gaagccaatt cagaaccact    5880
gcatagcagt gcttattatc ttatttatat gtagcaaaag gcacttaaat gatctcttat    5940
gacacatgcc agaaggaaaa caacagacta cacaattaca aggtcggaag ctacatagga    6000
ttaccataac agatagctga cggcctacaa aaaaagatag aatacaggag aacatcacac    6060
agataaaaac atatcaccct tgtactagca gggaggcggt gcttgctgga ttttagatca    6120
gttgcttgct ggattttaga tcagtacaca gtcctgccat caccatccag gatcatatcc    6180
ttgaaagccc caccattagg gatcataggc aacacatgct cctggtgtgg gacgattata    6240
tccaagaggt acggcctgg agtctcgagc atcttcttta tcgctgcgcg gacttcgttc    6300
ttctttgtca cacggaccgc tggaatgttg aacccttggg cgatcgtcac gaaatctgga    6360
tatatctcac tttcattctc tgggtttccc aagtatgtgt gcgctctgtt ggcctttag    6420 aacctgtcct cccactgcac caccatcccc aggtgctggt tgtttagcac aaagaccttc    6480
accgggaggt tctcaattcg gatcatagct agctcctgaa cgttcatgag aaagctacca    6540
tctccatcga tgtcaacaac agtaacacct gggttggcca cagaagcacc agcagcagcc    6600
```

```
ggcaaaccaa atcccatagc cccaagacca gctgaagaca accactgcct tggccgcttg    6660
taagtgtagt actgtgccgc ccacatctgg tgctgcccaa cacctgtgcc gatgatggcc    6720
tcgcctttcg tcagctcatc aagaacctga atagcatatt gtggctggat ctcctcatta    6780
gatgttttat acccaagggg gaattccctc ttctgctgat ccaactcatc gttccatgag    6840
ccaaagtcaa agctcttctt tgatgtgctt ccttcaagaa gagcattcat gccctgcaaa    6900
gcaagcttaa catctgcaca gatggacaca tgtggctgct tgttcttgcc aatctcagcc    6960
ggatcaatat caacgtgcac aatcttagcc ctgcttgcaa aagcctcaat cttccctgtc    7020
acacgatcat caaaccgcac accaagtgca agcaacagat cggccttatc cactgcataa    7080
tttgcataca ccgtgccatg catacctagc atgcgcagag acagtgggtc gtcgctgggg    7140
aagttgccga ggcccataag agtagttgtg accgggattc cagtcagctc cacaaagcgt    7200
cgcaactcct caccagatgc tgcgcagcca ccgccaacat aaagaacagg gcgccgggat    7260
tcaccaacaa gacgcagcac ctgctcaagc aactcagtcg caggggggctt gggaaggcgc    7320 gcaatgtacc caggcagact catgggcttg tcccagacag gcaccgccat ctgctgctgg    7380
atgtccttgg ggatgtcgac aagcaccggc cccggtcgac cagaggaggc gaggaagaaa    7440
gcctcctgca cgacgcgggg gatgtcgtcg acgtcgagga ccaggtagtt gtgcttggtg    7500
atggagcggt tgacctcgac gatgggcgtc tcctggaagg cgtcggtgcc aatcatgcgt    7560
cgcggcacct gtcccgtgat ggcgaccatg gggacggaat cgagcagcgc gtcggcgagc    7620
gcggagacaa ggttggtggc gccggggccg gaggtggcga tgcagacgcc gacgcggccc    7680
gaggagcgcg cgtagccgga ggccgcaaag gcctcccctt gctcgtggcg gaagaggtgg    7740
ttggcgatga cggggggagcg ggtgagtgcc tggtggatct ccatggacgc gccgccgggg    7800
taggcgaaga cgtcgcggac gccgcagcgc tcagggact cgacgaggat gtcggcgccc    7860
ttgcggggat cggtggggcc ccacggccgg agcggggtgg ccggggggagc catcggcatg    7920 gcgggtgacg ccgctgagca cctgatgggc gcggcgaggg cgcggcgggt ggccaggagg    7980
tgcgcccggc gcctcgcctt gggcgcagcg gtagtggcgc cagtgagcgc ggtagacgcg    8040
gcggcggcgg tggccatggt ttctagaact agtggatccc ccgggctgca gaagtaacac    8100
caaacaacag ggtgagcatc gacaaaagaa acagtaccaa gcaaataaat agcgtatgaa    8160
ggcagggcta aaaaaatcca catatagctg ctgcatatgc catcatccaa gtatatcaag    8220
atcaaaataa ttataaaaca tacttgttta ttataataga taggtactca aggttagagc    8280
atatgaatag atgctgcata tgccatcatg tatatgcatc agtaaaaccc acatcaacat    8340
gtatacctat cctagatcga tatttccatc catcttaaac tcgtaactat gaagatgtat    8400
gacacacaca tacagttcca aaattaataa atacaccagg tagtttgaaa cagtattcta    8460
ctccgatcta gaacgaatga acgaccgccc aaccacacca catcatcaca accaagcgaa    8520
caaaaagcat ctctgtatat gcatcagtaa aacccgcatc aacatgtata cctatcctag    8580
atcgatattt ccatccatca tcttcaattc gtaactatga atatgtatgg cacacacata    8640
cagatccaaa attaataaat ccaccaggta gtttgaaaca gaattctact ccgatctaga    8700
acgaccgccc aaccagacca catcatcaca accaagacaa aaaaagcat gaaaagatga    8760 cccgacaaac aagtgcacgg catatattga ataaaggaa aagggcaaac caaaccctat    8820
gcaacgaaac aaaaaaaatc atgaaatcga tcccgtctgc ggaacggcta gagccatccc    8880
aggattcccc aaagagaaac actggcaagt tagcaatcag aacgtgtctg acgtacaggt    8940
cgcatccgtg tacgaacgct agcagcacgg atctaacaca aacacggatc taacacaaac    9000
```

```
atgaacagaa gtagaactac cgggccctaa ccatggaccg gaacgccgat ctagagaagg    9060
tagagagggg ggggggggga ggacgagcgg cgtaccttga agcggaggtg ccgacgggtg    9120
gatttggggg agatctggtt gtgtgtgtgt gcgctccgaa caacacgagg ttggggaaag    9180
agggtgtgga gggggtgtct atttattacg gcgggcgagg aagggaaagc gaaggagcgg    9240
tgggaaagga atcccccgta gctgccggtg ccgtgagagg aggaggaggc cgcctgccgt    9300
gccggctcac gtctgccgct ccgccacgca atttctggat gccgacagcg gagcaagtcc    9360
aacggtggag cggaactctc gagagggtc cagaggcagc gacagagatg ccgtgccgtc    9420
tgcttcgctt ggcccgacgc gacgctgctg gttcgctggt tggtgtccgt tagactcgtc    9480
gacggcgttt aacaggctgg cattatctac tcgaaacaag aaaaatgttt ccttagtttt    9540
tttaatttct taaagggtat ttgtttaatt tttagtcact ttattttatt ctattttata    9600
tctaaattat taaataaaaa aactaaaata gagtttagt tttcttaatt tagaggctaa     9660
aatagaataa aatagatgta ctaaaaaaat tagtctataa aaaccattaa ccctaaaccc    9720
taaatggatg tactaataaa atggatgaag tattatatag gtgaagctat ttgcaaaaaa    9780
aaaggagaac acatgcacac taaaaagata aaactgtaga gtcctgttgt caaaatactc    9840
aattgtcctt tagaccatgt ctaactgttc atttatatga ttctctaaaa cactgatatt    9900
attgtagtac tatagattat attattcgta gagtaaagtt taaatatatg tataaagata    9960
gataaactgc acttcaaaca agtgtgacaa aaaaaatatg tggtaatttt ttataactta   10020
gacatgcaat gctcattatc tctagagagg ggcacgaccg ggtcacgctg cactgcagga   10080
attcgataaa ctatcagtgt ttgacaggat atattggcgg gtaaacctaa gagaaaagag   10140
cgtttattag aataatcgga tatttaaaag ggcgtgaaaa ggtttatccg ttcgtccatt   10200
tgtatgtgca tgccaaccac agggttcccc tcgggagtgc ttggcattcc gtgcgataat   10260
gacttctgtt caaccaccca aacgtcggaa agcctgacga cggagcagca ttccaaaaag   10320
atcccttggc tcgtctgggt cggctagaag gtcgagtggg ctgctgtggc ttgatccctc   10380
aacgcggtcg cggacgtagc gcagcgccga aaaatcctcg atcgcaaatc cgacgctgtc   10440
gaaaagcgtg atctgcttgt cgctcttcg gccgacgtcc tggccagtca tcacgcgcca    10500
aagttccgtc acaggatgat ctggcgcgag ttgctggatc tcgccttcaa tccgggtctg   10560
tggcgggaac tccacgaaaa tatccgaacg cagcaagatc gtcgaccaat tcttgaagac   10620
gaaagggcct cgtgatacgc ctatttttat aggttaatgt catgataata atggtttctt   10680
agacgtcagg tggcactttt cggggaaatg tgcgcggaac ccctatttgt ttatttttct   10740
aaatacattc aaatatgtat ccgctcatga gacaataacc ctgataaatg cttcaataat   10800
attgaaaaag gaagagtatg agtattcaac atttccgtgt cgcccttatt cccttttttg   10860
cggcattttg ccttcctgtt tttgctcacc cagaaacgct ggtgaaagta aaagatgctg   10920
aagatcagtt gggtgcacga gtgggttaca tcgaactgga tctcaacagc ggtaagatcc   10980
ttgagagttt tcgccccgaa gaacgttttc caatgatgag cacttttaaa gttctgctat   11040
gtggcgcggt attatcccgt gttgacgccg ggcaagagca actcggtcgc cgcatacact   11100
attctcagaa tgacttggtt gagtactcac cagtcacaga aaagcatctt acggatggca   11160
tgacagtaag agaattatgc agtgctgcca taaccatgag tgataacact gcggccaact   11220
tacttctgac aacgatcgga ggaccgaagg agctaaccgc ttttttgcac aacatggggg   11280
atcatgtaac tcgccttgat cgttgggaac cggagctgaa tgaagccata ccaaacgacg   11340
agcgtgacac cacgatgcct gcagggggg ggggggggg acatgaggtt gccccgtatt    11400
```

```
cagtgtcgct gatttgtatt gtctgaagtt gttttttacgt taagttgatg cagatcaatt    11460
aatacgatac ctgcgtcata attgattatt tgacgtggtt tgatggcctc cacgcacgtt    11520
gtgatatgta gatgataatc attatcactt tacgggtcct ttccggtgat ccgacaggtt    11580
acggggcggc gacctcgcgg gttttcgcta tttatgaaaa ttttccggtt taaggcgttt    11640
ccgttcttct tcgtcataac ttaatgtttt tatttaaaat accctctgaa agaaaggaa     11700 acgacaggtg ctgaaagcga gcttttttggc ctctgtcgtt tcctttctct gttttttgtcc  11760 gtggaatgaa caatggaacc cccccccccc ccccctgca gcaatggcaa caacgttgcg     11820
caaactatta actggcgaac tacttactct agcttcccgg caacaattaa tagactggat    11880
ggaggcggat aaagttgcag gaccacttct gcgctcggcc cttccggctg gctggtttat    11940
tgctgataaa tctggagccg gtgagcgtgg gtctcgcggt atcattgcag cactgggggcc   12000 agatggtaag ccctcccgta tcgtagttat ctacacgacg gggagtcagg caactatgga   12060
tgaacgaaat agacagatcg ctgagatagg tgcctcactg attaagcatt ggtaactgtc    12120
agaccaagtt tactcatata ctttttagat tgatttaaaa cttcattttt aatttaaaag    12180
gatctaggtg aagatccttt ttgataatct catgaccaaa atcccttaac gtgagttttc    12240
gttccactga gcgtcagacc ccgtagaaaa gatcaaagga tcttcttgag atcctttttt    12300
tctgcgcgta atctgctgct tgcaaacaaa aaaaccaccg ctaccagcgg tggtttgttt    12360
gccggatcaa gagctaccaa ctcttttttcc gaaggtaact ggcttcagca gagcgcagat    12420
accaaatact gtccttctag tgtagccgta gttaggccac cacttcaaga actctgtagc    12480
accgcctaca tacctcgctc tgctaatcct gttaccagtg gctgctgcca gtggcgataa    12540
gtcgtgtctt accgggttgg actcaagacg atagttaccg gataaggcgc agcggtcggg    12600
ctgaacgggg ggttcgtgca cacagcccag cttggagcga acgacctaca ccgaactgag    12660
atacctacag cgtgagctat gagaaagcgc cacgcttccc gaagggagaa aggcggacag    12720
gtatccggta agcggcaggg tcggaacagg agagcgcacg agggagcttc caggggggaaa   12780 cgcctggtat ctttatagtc ctgtcgggtt tcgccacctc tgacttgagc gtcgattttt    12840
gtgatgctcg tcagggggggc ggagcctatg gaaaaacgcc agcaacgcgg cctttttacg    12900
gttcctggcc ttttgctggc cttttgctca catgttcttt cctgcgttat ccctgattc     12960 tgtggataac cgtattaccg cctttgagtg agctgatacc gctcgccgca gccgaacgac    13020
cgagcgcagc gagtcagtga gcgaggaagc ggaagagcgc ctgatgcggt attttctcct    13080
tacgcatctg tgcggtattt cacaccgcat atggtgcact ctcagtacaa tctgctctga    13140
tgccgcatag ttaagccagt atacactccg ctatcgctac gtgactgggt catggctgcg    13200
ccccgacacc cgccaacacc cgctgacgcg ccctgacggg cttgtctgct cccggcatcc    13260
gcttacagac aagctgtgac cgtctccggg agctgcatgt gtcagaggtt ttcaccgtca    13320
tcaccgaaac gcgcgaggca gcagatcccc cgatcaagta gatacactac atatatctac    13380
aatagacatc gagccggaag gtgatgttta ctttcctgaa atcccagca attttaggcc      13440 agttttttacc caagacttcg cctctaacat aaattatagt taccaaatct ggcaaaaggg    13500
ttaacaagtg gcagcaacgg attcgcaaac ctgtcacgcc ttttgtgcca aaagccgcgc    13560
caggtttgcg atccgctgtg ccaggcgtta ggcgtcatat gaagatttcg gtgatccctg    13620
agcaggtggc ggaaacattg gatgctgaga accatttcat tgttcgtgaa gtgttcgatg    13680
tgcacctatc cgaccaaggc tttgaactat ctaccagaag tgtgagcccc taccggaagg    13740
attacatctc ggatgatgac tctgatgaag actctgcttg ctatggcgca ttcatcgacc    13800
```

```
aagagcttgt cgggaagatt gaactcaact caacatggaa cgatctagcc tctatcgaac    13860
acattgttgt gtcgcacacg caccgaggca aaggagtcgc gcacagtctc atcgaatttg    13920
cgaaaaagtg ggcactaagc agacagctcc ttggcatacg attagagaca caaacgaaca    13980
atgtacctgc ctgcaatttg tacgcaaaat gtggctttac tctcggcggc attgacctgt    14040
tcacgtataa aactagacct caagtctcga acgaaacagc gatgtactgg tactggttct    14100
cgggagcaca ggatgacgcc taacaattca ttcaagccga caccgcttcg cggcgcggct    14160
taattcagga gttaaacatc atgagggaag cggtgatcgc cgaagtatcg actcaactat    14220
cagaggtagt tggcgtcatc gagcgccatc tcgaaccgac gttgctggcc gtacatttgt    14280
acggctccgc agtggatggc ggcctgaagc cacacagtga tattgatttg ctggttacgg    14340
tgaccgtaag gcttgatgaa caacgcggc gagctttgat caacgacctt ttggaaactt    14400
cggcttcccc tggagagagc gagattctcc gcgctgtaga agtcaccatt gttgtgcacg    14460
acgacatcat tccgtggcgt tatccagcta agcgcgaact gcaatttgga gaatggcagc    14520
gcaatgacat tcttgcaggt atcttcgagc cagccacgat cgacattgat ctggctatct    14580
tgctgacaaa agcaagagaa catagcgttg ccttggtagg tccagcggcg gagaactct    14640 ttgatccggt tcctgaacag gatctatttg aggcgctaaa tgaaaccttta acgctatgga    14700 actcgccgcc cgactgggct ggcgatgagc gaaatgtagt gcttacgttg tcccgcattt    14760
ggtacagcgc agtaaccggc aaaatcgcgc cgaaggatgt cgctgccgac tgggcaatgg    14820
agcgcctgcc ggcccagtat cagcccgtca tacttgaagc taggcaggct tatcttggac    14880
aagaagatcg cttggcctcg cgcgcagatc agttggaaga atttgttcac tacgtgaaag    14940
gcgagatcac caaggtagtc ggcaaataat gtctaacaat tcgttcaagc cgacgccgct    15000
tcgcggcgcg gcttaactca agcgttagag agctggggaa gactatgcgc gatctgttga    15060
aggtggttct aagcctcgta cttgcgatgg catcggggca ggcacttgct gacctgccaa    15120 ttgtttttagt ggatgaagct cgtcttccct atgactactc cccatccaac tacgacattt    15180
ctccaagcaa ctacgacaac tccataagca attacgacaa tagtccatca aattacgaca    15240
actctgagag caactacgat aatagttcat ccaattacga caatagtcgc aacggaaatc    15300
gtaggcttat atatagcgca aatgggtctc gcactttcgc cggctactac gtcattgcca    15360
acaatgggac aacgaacttc ttttccacat ctggcaaaag gatgttctac accccaaaag    15420 ggggcgcgg cgtctatggc ggcaaagatg ggagcttctg cggggcattg gtcgtcataa    15480
atggccaatt ttcgcttgcc ctgacagata acggcctgaa gatcatgtat ctaagcaact    15540
agcctgctct ctaataaaat gttaggcctc aacatctagt cgcaagctga ggggaaccac    15600
tagtgtcata cgaacctcca agagacggtt acacaaacgg gtacattgtt gatgtcatgt    15660
atgacaatcg cccaagtaag tatccagctg tgttcagaac gtacgtccga attaattcat    15720
cggggtacgg tcgacgatcg tcaacgttca cttctaaaga aatagcgcca ctcagcttcc    15780
tcagcggctt tatccagcga tttcctatta tgtcggcata gttctcaaga tcgacagcct    15840
gtcacggtta agcgagaaat gaataagaag gctgataatt cggatctctg cgagggagat    15900
gatatttgat cacaggcagc aacgctctgt catcgttaca atcaacatgc tacccctccgc    15960 gagatcatcc gtgtttcaaa cccggcagct tagttgc                              15997
```

<210> SEQ ID NO 2
<211> LENGTH: 1917
<212> TYPE: DNA
<213> ORGANISM: Zea mays

```
<220> FEATURE:
<221> NAME/KEY: CDS
<222> LOCATION: (1)..(1914)
<223> OTHER INFORMATION: coding for ahas XA17 mutant
<220> FEATURE:
<221> NAME/KEY: mutation
<222> LOCATION: (1625)..(1625)
<223> OTHER INFORMATION: G / T mutation conferring XA17 phenotype
      resulting in Tryptophane to Leucine change at position 542 of
      translated amino acid sequence

<400> SEQUENCE: 2
```

| | | | | | | | | | | | | | | | | |
|---|---|---|---|---|---|---

| | | |
|---|---|---|
| tat gtt ggc ggt ggc tgc gca gca tct ggt gag gag ttg cga cgc ttt<br>Tyr Val Gly Gly Gly Cys Ala Ala Ser Gly Glu Glu Leu Arg Arg Phe<br>           275                 280                285 | | 864 |
| gtg gag ctg act gga atc ccg gtc aca act act ctt atg ggc ctc ggc<br>Val Glu Leu Thr Gly Ile Pro Val Thr Thr Thr Leu Met Gly Leu Gly<br>       290                 295                 300 | | 912 |
| aac ttc ccc agc gac gac cca ctg tct ctg cgc atg cta ggt atg cat<br>Asn Phe Pro Ser Asp Asp Pro Leu Ser Leu Arg Met Leu Gly Met His<br>305                 310                 315                320 | | 960 |
| ggc acg gtg tat gca aat tat gca gtg gat aag gcc gat ctg ttg ctt<br>Gly Thr Val Tyr Ala Asn Tyr Ala Val Asp Lys Ala Asp Leu Leu Leu<br>                 325                 330                335 | | 1008 |
| gca ctt ggt gtg cgg ttt gat gat cgt gtg aca ggg aag att gag gct<br>Ala Leu Gly Val Arg Phe Asp Asp Arg Val Thr Gly Lys Ile Glu Ala<br>                 340                 345                350 | | 1056 |
| ttt gca agc agg gct aag att gtg cac gtt gat att gat ccg gct gag<br>Phe Ala Ser Arg Ala Lys Ile Val His Val Asp Ile Asp Pro Ala Glu<br>                 355                 360                365 | | 1104 |
| att ggc aag aac aag cag cca cat gtg tcc atc tgt gca gat gtt aag<br>Ile Gly Lys Asn Lys Gln Pro His Val Ser Ile Cys Ala Asp Val Lys<br>370                 375                 380 | | 1152 |
| ctt gct ttg cag ggc atg aat gct ctt ctt gaa gga agc aca tca aag<br>Leu Ala Leu Gln Gly Met Asn Ala Leu Leu Glu Gly Ser Thr Ser Lys<br>385                 390                 395                400 | | 1200 |
| aag agc ttt gac ttt ggc tca tgg aac gat gag ttg gat cag cag aag<br>Lys Ser Phe Asp Phe Gly Ser Trp Asn Asp Glu Leu Asp Gln Gln Lys<br>                 405                 410                415 | | 1248 |
| agg gaa ttc ccc ctt ggg tat aaa aca tct aat gag gag atc cag cca<br>Arg Glu Phe Pro Leu Gly Tyr Lys Thr Ser Asn Glu Glu Ile Gln Pro<br>                 420                 425                430 | | 1296 |
| caa tat gct att cag gtt ctt gat gag ctg acg aaa ggc gag gcc atc<br>Gln Tyr Ala Ile Gln Val Leu Asp Glu Leu Thr Lys Gly Glu Ala Ile<br>                 435                 440                445 | | 1344 |
| atc ggc aca ggt gtt ggg cag cac cag atg tgg gcg gca cag tac tac<br>Ile Gly Thr Gly Val Gly Gln His Gln Met Trp Ala Ala Gln Tyr Tyr<br>450                 455                 460 | | 1392 |
| act tac aag cgg cca agg cag tgg ttg tct tca gct ggt ctt ggg gct<br>Thr Tyr Lys Arg Pro Arg Gln Trp Leu Ser Ser Ala Gly Leu Gly Ala<br>465                 470                 475                480 | | 1440 |
| atg gga ttt ggt ttg ccg gct gct gct ggt gct tct gtg gcc aac cca<br>Met Gly Phe Gly Leu Pro Ala Ala Ala Gly Ala Ser Val Ala Asn Pro<br>                 485                 490                495 | | 1488 |
| ggt gtt act gtt gtt gac atc gat gga gat ggt agc ttt ctc atg aac<br>Gly Val Thr Val Val Asp Ile Asp Gly Asp Gly Ser Phe Leu Met Asn<br>                 500                 505                510 | | 1536 |
| gtt cag gag cta gct atg atc cga att gag aac ctc ccg gtg aag gtc<br>Val Gln Glu Leu Ala Met Ile Arg Ile Glu Asn Leu Pro Val Lys Val<br>                 515                 520                525 | | 1584 |
| ttt gtg cta aac aac cag cac ctg ggg atg gtg gtg cag ttg gag gac<br>Phe Val Leu Asn Asn Gln His Leu Gly Met Val Val Gln Leu Glu Asp<br>530                 535                 540 | | 1632 |
| agg ttc tat aag gcc aac aga gcg cac aca tac ttg gga aac cca gag<br>Arg Phe Tyr Lys Ala Asn Arg Ala His Thr Tyr Leu Gly Asn Pro Glu<br>545                 550                 555                560 | | 1680 |

```
aat gaa agt gag ata tat cca gat ttc gtg acg atc gcc aaa ggg ttc    1728
Asn Glu Ser Glu Ile Tyr Pro Asp Phe Val Thr Ile Ala Lys Gly Phe
            565                 570                 575 aac att cca gcg gtc cgt gtg aca aag aag aac gaa gtc cgc gca gcg    1776
Asn Ile Pro Ala Val Arg Val Thr Lys Lys Asn Glu Val Arg Ala Ala
        580                 585                 590 ata aag aag atg ctc gag act cca ggg ccg tac ctc ttg gat ata atc    1824
Ile Lys Lys Met Leu Glu Thr Pro Gly Pro Tyr Leu Leu Asp Ile Ile
    595                 600                 605 gtc cca cac cag gag cat gtg ttg cct atg atc cct agt ggt ggg gct    1872
Val Pro His Gln Glu His Val Leu Pro Met Ile Pro Ser Gly Gly Ala
610                 615                 620 ttc aag gat atg atc ctg gat ggt gat ggc agg act gtg tac tga        1917
Phe Lys Asp Met Ile Leu Asp Gly Asp Gly Arg Thr Val Tyr
625                 630                 635

<210> SEQ ID NO 3
<211> LENGTH: 638
<212> TYPE: PRT
<213> ORGANISM: Zea mays

<400> SEQUENCE: 3
```

Met Ala Thr Ala Ala Ala Ala Ser Thr Ala Leu Thr Gly Ala Thr Thr
1               5                   10                  15

Ala Ala Pro Lys Ala Arg Arg Arg Ala His Leu Leu Ala Thr Arg Arg
            20                  25                  30

Ala Leu Ala Ala Pro Ile Arg Cys Ser Ala Ala Ser Pro Ala Met Pro
        35                  40                  45

Met Ala Pro Pro Ala Thr Pro Leu Arg Pro Trp Gly Pro Thr Asp Pro
    50                  55                  60

Arg Lys Gly Ala Asp Ile Leu Val Glu Ser Leu Glu Arg Cys Gly Val
65                  70                  75                  80

Arg Asp Val Phe Ala Tyr Pro Gly Gly Ala Ser Met Glu Ile His Gln
                85                  90                  95

Ala Leu Thr Arg Ser Pro Val Ile Ala Asn His Leu Phe Arg His Glu
            100                 105                 110

Gln Gly Glu Ala Phe Ala Ala Ser Gly Tyr Ala Arg Ser Ser Gly Arg
        115                 120                 125

Val Gly Val Cys Ile Ala Thr Ser Gly Pro Gly Ala Thr Asn Leu Val
    130                 135                 140

Ser Ala Leu Ala Asp Ala Leu Leu Asp Ser Val Pro Met Val Ala Ile
145                 150                 155                 160

Thr Gly Gln Val Pro Arg Arg Met Ile Gly Thr Asp Ala Phe Gln Glu
                165                 170                 175

Thr Pro Ile Val Glu Val Thr Arg Ser Ile Thr Lys His Asn Tyr Leu
            180                 185                 190

Val Leu Asp Val Asp Asp Ile Pro Arg Val Val Gln Glu Ala Phe Phe
        195                 200                 205

Leu Ala Ser Ser Gly Arg Pro Gly Pro Val Leu Val Asp Ile Pro Lys
    210                 215                 220

Asp Ile Gln Gln Gln Met Ala Val Pro Val Trp Asp Lys Pro Met Ser
225                 230                 235                 240

Leu Pro Gly Tyr Ile Ala Arg Leu Pro Lys Pro Pro Ala Thr Glu Leu
                245                 250                 255

Leu Glu Gln Val Leu Arg Leu Val Gly Glu Ser Arg Arg Pro Val Leu
            260                 265                 270

Tyr Val Gly Gly Gly Cys Ala Ala Ser Gly Glu Glu Leu Arg Arg Phe

```
               275                 280                 285
        Val Glu Leu Thr Gly Ile Pro Val Thr Thr Thr Leu Met Gly Leu Gly
            290                 295                 300

Asn Phe Pro Ser Asp Asp Pro Leu Ser Leu Arg Met Leu Gly Met His
        305                 310                 315                 320

Gly Thr Val Tyr Ala Asn Tyr Ala Val Asp Lys Ala Asp Leu Leu Leu
                        325                 330                 335

Ala Leu Gly Val Arg Phe Asp Asp Arg Val Thr Gly Lys Ile Glu Ala
                    340                 345                 350

Phe Ala Ser Arg Ala Lys Ile Val His Val Asp Ile Asp Pro Ala Glu
                355                 360                 365

Ile Gly Lys Asn Lys Gln Pro His Val Ser Ile Cys Ala Asp Val Lys
            370                 375                 380

Leu Ala Leu Gln Gly Met Asn Ala Leu Leu Glu Gly Ser Thr Ser Lys
        385                 390                 395                 400

Lys Ser Phe Asp Phe Gly Ser Trp Asn Asp Glu Leu Asp Gln Gln Lys
                        405                 410                 415

Arg Glu Phe Pro Leu Gly Tyr Lys Thr Ser Asn Glu Glu Ile Gln Pro
                    420                 425                 430

Gln Tyr Ala Ile Gln Val Leu Asp Glu Leu Thr Lys Gly Glu Ala Ile
                435                 440                 445

Ile Gly Thr Gly Val Gly Gln His Gln Met Trp Ala Ala Gln Tyr Tyr
            450                 455                 460

Thr Tyr Lys Arg Pro Arg Gln Trp Leu Ser Ser Ala Gly Leu Gly Ala
        465                 470                 475                 480

Met Gly Phe Gly Leu Pro Ala Ala Ala Gly Ala Ser Val Ala Asn Pro
                        485                 490                 495

Gly Val Thr Val Val Asp Ile Asp Gly Asp Gly Ser Phe Leu Met Asn
                    500                 505                 510

Val Gln Glu Leu Ala Met Ile Arg Ile Glu Asn Leu Pro Val Lys Val
                515                 520                 525

Phe Val Leu Asn Asn Gln His Leu Gly Met Val Val Gln Leu Glu Asp
            530                 535                 540

Arg Phe Tyr Lys Ala Asn Arg Ala His Thr Tyr Leu Gly Asn Pro Glu
        545                 550                 555                 560

Asn Glu Ser Glu Ile Tyr Pro Asp Phe Val Thr Ile Ala Lys Gly Phe
                        565                 570                 575

Asn Ile Pro Ala Val Arg Val Thr Lys Lys Asn Glu Val Arg Ala Ala
                    580                 585                 590

Ile Lys Lys Met Leu Glu Thr Pro Gly Pro Tyr Leu Leu Asp Ile Ile
                595                 600                 605

Val Pro His Gln Glu His Val Leu Pro Met Ile Pro Ser Gly Gly Ala
            610                 615                 620

Phe Lys Asp Met Ile Leu Asp Gly Asp Gly Arg Thr Val Tyr
        625                 630                 635
```